(12) United States Patent
McLachlan

(10) Patent No.: US 7,094,949 B2
(45) Date of Patent: *Aug. 22, 2006

(54) BREEDING AND MILKING COWS FOR MILK FREE OF β-CASEIN A$^1$

(75) Inventor: Corran Norman Stuart McLachlan, North Shore (NZ)

(73) Assignee: A2 Corporation Limited, Auckland (NZ)

( * ) Notice: Subject to any disclaimer, the term of this patent is extended or adjusted under 35 U.S.C. 154(b) by 305 days.

This patent is subject to a terminal disclaimer.

(21) Appl. No.: 10/369,679

(22) Filed: Feb. 21, 2003

(65) Prior Publication Data

US 2003/0221200 A1 Nov. 27, 2003

Related U.S. Application Data

(63) Continuation-in-part of application No. 09/906,614, filed on Jul. 18, 2001, now abandoned, which is a continuation of application No. 09/500,801, filed on Feb. 10, 2000, now abandoned, which is a continuation of application No. 08/645,219, filed on May 13, 1996, now abandoned.

(30) Foreign Application Priority Data

May 16, 1995 (NZ) ..................... 272133

(51) Int. Cl.
*A01K 67/00* (2006.01)
*A61K 35/20* (2006.01)
*A23G 1/00* (2006.01)
*A23C 9/154* (2006.01)
*C12Q 1/68* (2006.01)

(52) U.S. Cl. ............................ 800/22; 800/8; 424/535; 426/491; 426/580; 435/6

(58) Field of Classification Search ................ 435/6, 435/580; 424/535; 800/8, 22; 426/491, 426/580
See application file for complete search history.

(56) References Cited

U.S. PATENT DOCUMENTS

| 5,106,618 A | 4/1992 | Beck et al. |
| 6,451,368 B1 * | 9/2002 | Elliott et al. ................. 426/580 |
| 6,570,060 B1 * | 5/2003 | McLachlan ..................... 800/8 |

FOREIGN PATENT DOCUMENTS

| EP | 0 631 731 | 1/1995 |
| WO | WO 95/10192 | 4/1995 |
| WO | WO 96/14577 | 5/1996 |

OTHER PUBLICATIONS

Hill, J.P. The Influence of Consumption of A1 β-Casein on Heart Disease. New Zealand Medical Journal. Feb. 2003, vol. 116, No. 1169, pp. 1 and 2.*

Swinburn, B. Beta Casein A1 and A2 in Milk and Human Health. Report to New Zealand Food Safety Authority, „Jul. 13, 2004.*

Beales et al., "A multi-centre, blinded international trial of the effect of A$^1$ and A$^2$ β-casein variants on diabetes incidence in two rodent models of spontaneous Type I diabetes", Diabetologica, 2002, 45: pp. 1240-1246.

Laugesen et al., "Ischaemic heart disease, Type 1 diabetes, and cow milk A1 β-casein", New Zealand Medical Journal, vol. 116 No. 1168, ISSN 1175 8716, 2003, pp. 1-19.

MacLachlan et al., "Heart Disease, Diabetes, Gut Immune Suppression and Epidemiology Studies", Journal of Nutritional & Environmental Medicine, 2002, 12(3): pp. 197-206.

Tailford et al., "A casein variantt in cow's milk is atherogenic", Atherosclerosis, 2003, pp. 13-19.

AS Truswell, "REVIEW—The A2 milk case: a critical review", European Journal of Clinical Nutrition (2005), 59, pp. 623-631.

K.F. Ng Kwai Hang, "Genetic Polymorphism of Milk Proteins: Influence on Milk Yield and Composition", Bulletin of the IDF 304, 1987, pp. 6-7.

Ng-Kwai-Hang et al., "Association Between Genetic Polymerphism of Milk Proteins and Production Traits During Three Lactations", Journal of Dairy Science, vol. 73, No. 12, 1990, pp. 3414-3420.

Van Eenennaam et al., "Milk Protein Polymorphisms in California Dairy Cattle", Journal of Dairy Science, vol. 374, No. 5, 1991, pp. 1730-1742.

Fehily et al., "Diet and incident ischaemic heart disease: the Caerphilly Study", British Journal of Nutrition, 1993, vol. 69, pp. 303-314.

McLean et al., "Effects of milk protein genetic variants on milk yield and composition", Journal of Dairy Research, vol. 51, 1984, pp. 531-546.

Aleandri et al., "The Effects of Milk Protein Polymorphisms on Milk Components and Cheese-Producing Ability", Journal of Dairy Science, vol. 73, No. 2, 1990, pp. 241-255.

Wong et al., Fundamentals of Dairy Chemistry, Third Edition, Chapter 2, Van Nostrand Reinhold, New York, 1988.

Bovenhuis et al., "Estimation of Milk Protein Gene Frequencies in Crossbred Cattle by Maximum Likelihood Method", Journal of Dairy Science, 74:2728, 1991, pp. 2549-2559.

Gonyon et al., "Associations of Bovine Blood and Milk Polymorphisms with Lactation Traits: Holsteins", Journal of Dairy Science, vol. 70, No. 12, 1987, pp. 2585-2598.

(Continued)

*Primary Examiner*—Deborah Crouch
(74) *Attorney, Agent, or Firm*—Young & Thompson

(57) ABSTRACT

A milk or other dairy product, capable of minimizing the onset of disease such as coronary heart disease or enhancing the immune response is derived from animals which are substantially free of the β-casein A$^1$ allele. Bulk milk can be produced by testing for and culling cows who test positive for the β-casein A$^1$ allele, or by producing immunoglobulins and other immune response proteins, in cow's milk from animals not possessing the β-casein A$^1$ allele, or other commercial milk producing animals, to this allele, to counteract the immnunosuppressant substances present that are produced from it, in commercial milking cows such as Holsteins, together with its blending with non-treated milk or the recovery of such immunoproteins.

19 Claims, 12 Drawing Sheets

OTHER PUBLICATIONS

Biss et al., "Some Unique Biologic Characteristics of the Masai of East Africa", The New England Journal of Medicine, vol. 284, No. 13, Apr. 1, 1997, pp. 694-699.

Shaper, "Cardiovascular studies in the Samburu tribe of Northern Kenya", Am. Heart J., Apr. 1962, pp. 437-442.

R.J. Wall, "Transgenic Livestock: Progress and Prospects for the Future", Theriogenelogy, vol. 45, 1996, pp. 57-68.

L. Houdebine, "Production of pharmaceutical proteins from transgenic animals", Journal of Biotechnology, pp. 269-287.

M. Baringa et al., "Knockout Mice: Round Two", Science, vol. 265, Jul. 1994, pp. 26-27.

Y. Kawamoto et al., "A Population Genetic Study on Yaks, Cattle and Their Hybrids in Nepal Using Milk Protein Variations", Animal Science Technology, vol. 63, No. 6, 1992, pp. 563-575.

E. Jakob et al., "Implications of Genetic Polymorphism of Milk Proteins on Production and Processing of Milk", *Bulletin of the IDF 304*, 1987, pp. 2-3, and 6-8.

John R. Campbell et al., "The Science of Providing Milk for Man", McGraw-Hill Book Co., 1975, pp. 3,31, 131-132, 252-253, 352, 545 and 616-617.

Ng-Kwai-Hang et al.; Genetic Polymorphism of Milk Proteins, In Advanced Dairy Chemistry; 1 Proteins, P.F. Fox, ed. Elsevier, London, 1994.

Campbell et al.; The Science of Providing Milk for Man, 1975 at pp. 3, 31, 131-132, 252-253, 352, 545 and 616-617.

Ng-Kwai-Hang et al.; Associated Between Genetic Polymorphisms of Milk Proteins and Production Rates During Three Lactations, 1990, J. Dairy Science 13: 3414-3420.

* cited by examiner

A¹ and A² Amplicons for the ACRS Genotyping Method

```
                        |------Casein Dde2 primer------|
A² Amplicon          5' GAGTAAGAGGAGGGATGTTTTGTGGGAGGCTCTtagggatgggcc.....'
A² template 3'  ..ccaaactcattctctcccctacaaaacaccctccgacaatccctaccccggttccn......

|------Casein Dde2 primer------|
A¹ Amplicon          5' GAGTAAGAGAGGAGGGATGTTTTGTGGGAGGCTCTtagtgatgggccc.....'
A¹ template 3'  ..cccaaactcattctctcccctacaaaacaccctccgacaatacctaccccggttccc......
```

FIG. 5

Electrophoresis Results for the ACRS Genotyping Method

FIG. 7

Gene Fragment Amplified in the Primer Extension Genotyping Method

5'ACTGGATTATGGACTCAAAGATTTGTTTTCCTTCTTTCCAGGATGAACTCCGGAT
AAAATCCACCCCTTTGCCCAGACACAGTCTCTAGTCTATCCCTTCCCTGGGCCCAT
CC[A/C]TAACAGCCTCCCACAAAACATCCCTCCTCTTACTCAAACCCCTGTGGTG
GTGCCGCCTTTCCTTCAGCCTGAAGTAATGGGAGTCTCCAAAGTGAAGGAGGCTA
TGGCTCCTAAGCA[A/C]AAAGAAATGCCCTTCCCTAAATATCCAGTTGAGCCCTTT
ACTGAAAG[C/G]CAGAGCCTGACTCTCACTGATGTTGAAAATCTGCACCTT-3'

Mass Spectrometry Profile Results for the Primer Extension Genotyping Method

A.

Table of Significance (P<0.05)

| Group | Is significantly different from Group |
|---|---|
| 1 | 2, 4, 5, 7, 10 |
| 2 | 1, 9, 10 |
| 3 | 1, 9, 10 |
| 4 | 1, 9, 10 |
| 5 | 1, 9, 10 |
| 6 | 1, 9, 10 |
| 7 | 1, 9, 10 |
| 8 | 1, 9, 10 |
| 9 | 2, 4, 5, 7, 10 |
| 10 | 1, 2, 3, 4, 5, 6, 7, 8, 9 |

Table of Significance (P<0.05)

| Group | Is significantly different from Group |
|---|---|
| 1 | 10 |
| 2 | 10 |
| 3 | 10 |
| 4 | 10 |
| 5 | 10 |
| 6 | 10 |
| 7 | 10 |
| 8 | 10 |
| 9 | 10 |
| 10 | 1, 2, 3, 4, 5, 6, 7, 8, 9 |

BREEDING AND MILKING COWS FOR MILK FREE OF β-CASEIN A¹

FIELD OF THE INVENTION

This invention relates to milk free of the β-casein A¹ protein. Such milk is useful for the prevention or treatment of coronary heart disease. In particular, the invention relates to the breeding of bovine bulls that do not have DNA encoding for β-casein A¹ with bovine cows that do not have DNA encoding for β-casein A¹ and then milking the progeny cows. The milk produced is free of β-casein A¹.

BACKGROUND OF THE INVENTION

Coronary heart disease is a major cause of death, particularly in western world countries where the populations are generally well-nourished. Many factors are implicated as risk factors for this disease including obesity, smoking, genetic predisposition, diet, hypertension, and cholesterol.

Dairy products, especially milk, are a major contributor to the dietary intake of humans, again particularly in western world populations. Milk contains numerous components of nutritional and health benefit. Calcium is one example. However, milk is also a significant source of dietary fat. It is widely accepted that saturated fats found in milk are a risk factor for coronary heart disease. However, an additional risk factor present in some bovine milk unrelated to the fat content has been discovered. What is entirely surprising is the source of the risk. The source is not dependent on the fat content of milk. Instead, it is a milk protein, β-casein, which is linked to coronary heart disease.

A number of variants of milk proteins have been identified. Initially, three variants of β-casein were discovered (Aschaffenburg, 1961) and were denoted A, B and C. It was later found that the A variant could be resolved into $A^1$, $A^2$ and $A^3$ by gel electrophoresis (Peterson et. al. 1966). The β-casein variants now known are $A^1$, $A^2$, $A^3$, B, C, D, E and F, with $A^1$ and $A^2$ being present in milk in the highest proportions. It is anticipated that other variants may be identified in the future.

The milk protein β-casein $A^1$ has been determined to represent the risk factor in bovine milk that is linked to coronary heart disease, or at least is the principal risk factor. This determination forms the basis of the present invention.

There is no relationship between the fat content of milk and β-casein genotype in cows. Therefore, selecting cattle on the basis of milk fat content will not identify which bovines produce the novel risk factor, namely the specific β-casein variant, in their milk.

There is no significant difference in the fat content of milk produced by cows which are homozygous for the β-casein $A^1$ allele (i.e. $A^1A^1$) and cows which are homozygous for the β-casein $A^2$ allele (i.e. $A^2A^2$). This is apparent from studies reported in the literature.

Ng-Kwai-Hang has carried out several studies. One study (Ng-Kwai-Hang et. al., 1990) suggested that milk containing β-casein $A^1$ rather than β-casein $A^2$ may have a slightly higher fat content. However, these differences were very small. The differences between milk from $A^1$ homozygous cows and milk from $A^2$ homozygous cows were 0.05% (for the first lactation period), 0.07% (for the second lactation period), and 0.04% (for the third lactation period).

In another study (in 1995), Ng-Kwai-Hang (in an abstract cited by Jakob et. al., 1997) found the opposite effect (i.e. the $A^1A^1$ product had a lower fat content than the $A^2A^2$ product). Thus, the 1995 Ng-Kwai-Hang study directly contradicts the Ng-Kwai-Hang, et. al., 1990 study.

McLean et. al., 1984 (McLean) also reported that there was no significant difference in the fat content of milk from cows of $A^1A^1$ and $A^2A^2$ genotypes (mean±standard error: 45.8±2.6 g/l for milk of $A^1A^1$ cows and 48.6±1.9 g/l for milk of $A^2A^2$ cows).

Aleandri et al., 1990 (Aleandri), shows in Table 5 that the least squares estimates of the effects of different genotypes and their standard errors on fat percentage in milk are 0.12±0.09 for $A^1A^1$ cows and 0.07±0.09 for $A^2A^2$ cows. Taking into account the standard error for the test, Aleandri indicates that the effects of $A^1A^1$ and $A^2A^2$ genotypes on milk fat content are equivalent.

Bovenhuis et. al., 1992 (Bovenhuis), highlights statistical problems associated with the way in which the genotype effects on fat percentages in milk are studied and documented. It is stated that the ordinary least squares estimates may be biased. Bovenhuis points out that the analysis of the effect of a particular genotype on various characteristics of milk is complex in nature and may, among other things, be affected by other genes which may be linked to the gene under study. Bovenhuis attempts to take into account the above variables and to overcome statistical problems by using an animal model method.

Table 3 of Bovenhuis indicates that, for a statistical model in which each milk protein gene is analysed separately and the $A^1A^1$ cows designated as being the standard (i.e. given a value of 0% fat attributable to the genotype), the $A^2A^2$ genotype was estimated not to contribute (i.e. 0%) to the fat content of the milk of the animals harbouring that genotype when compared to the $A^1A^1$ genotype. The standard error of the test is recorded as 0.02%. Where a statistical model was used in which all milk protein genes were analysed simultaneously (Table 4 of Bovenhuis) and the $A^1A^1$ genotype was again designated as being the standard (at 0% fat content attributable to the $A^1A^1$ genotype), the $A^2A^2$ genotype was estimated to contribute to the fat content of the milk at −0.01% when compared with the $A^1A^1$ genotype. In this study a standard error of 0.02 was designated. Taking into account the standard error of the tests these results indicate that the $A^2A^2$ genotype contributes to the fat content of milk in an equivalent manner to the genotype $A^1A^1$. Gonyon et. al., 1987 (Gonyon) reached the same conclusion as Bovenhuis.

The level of individual components in milk is influenced by both the genotype and the environment. That is, the variation between animals in milk output or milk composition is due to both genotypic and phenotypic factors. For example, Bassette et. al., 1988 (Bassette) indicates that the composition of bovine milk may be influenced by a number of environmental factors and conditions other than genetic factors. Environmental factors may impact on milk production and the constituents contained within the milk (including fat content). For example, changes in milk composition occur due to:

the stage of lactation (e.g., the fat content of colostrum is often higher; the concentration of fat changes over a period of many weeks as the cow goes through lactation);

the age of the cow and the number of previous lactations;

the nutrition of the cow including the type and composition of feed consumed by the cow;

seasonal variations;

the environmental temperature at which the cows are held;

variations due to the milking procedure (e.g., the fat content of milk tends to increase during the milking process which means that for an incomplete milking the fat content would generally be lower than normal and for a complete milking the fat content will be higher than normal); and milking at different times of the day.

It is therefore apparent from the studies in this field that a person skilled in the relevant area of technology would not find a link between the fat content of milk and the β-casein genotype of the milk-producing bovines from which that milk is produced. The milk protein β-casein A¹ has now been identified as a risk factor linked to coronary heart disease in its own right.

Epidemiological evidence strongly suggests that dietary β-casein A¹ is harmful to human health. For example, WO 96/14577 describes the impact of β-casein A¹ on Type I diabetes. The epidemiological evidence suggests that β-casein A¹ stimulates diabetogenic activity in humans. Furthermore, WO 96/14577 describes the induction of autoimmune, or Type I, diabetes in the non-obese diabetic (NOD) mouse model by way of consumption of β-casein A¹. The invention described focuses on reducing the risk of contracting Type I diabetes in a susceptible individual by restricting the milk or milk product intake of that individual to milk containing only non-diabetogenic β-casein variants.

Beales et al., 2002 (Beales) describes an investigation of whether β-casein A¹ is more diabetogenic than β-casein A². The results were not conclusive, although β-casein A¹ was found to be more diabetogenic than β-casein A² in certain rats (BB rats) fed a soy isolate based infant formula (ProSobee).

WO 96/36239 is the PCT publication for PCT/NZ96/00029 from which U.S. Ser. No. 09/906,614 and this application are derived. WO 96/36239 advocates the avoidance of β-casein A¹ in the human diet. Epidemiological evidence establishes a correlation between the consumption of β-casein A¹ in various populations and the incidence of coronary heart disease. In particular, the invention of U.S. Ser. No. 09/906,614 focuses on the avoidance of β-casein A¹ by selecting milking cows by testing genetic material for DNA encoding the various β-caseins.

McLachlan, 2001 (McLachlan) presents data reporting the link between the consumption of β-casein A¹ and both type 1 diabetes and coronary heart disease.

Thus, the link between β-casein A¹ and diabetes and the link between β-casein A¹ and coronary heart disease have both been well documented. Additionally, it has recently been shown that the deleterious effects of β-casein A¹ now extend to neurological disorders. WO 02/19832 describes the avoidance of inducing or aggravating a neurological or mental disorder by providing milk which does not contain any "histidine variant". A histidine variant is defined in that document as a β-casein variant which has histidine at position 67. β-Casein A¹ is such a histidine variant.

WO 01/00047 discloses a dietary supplement comprising a milk product which contains predominantly the A² variant of the β-caseins, and which is fortified with a compound (or compounds) that lowers human plasma homocyst(e)ine levels. Such compounds may include betaine, cobalamin, folic acid or pyridoxine. Two possible advantages to this are described. Firstly, the replacement of β-casein A¹ in the supplement with β-casein A² will lower the risk of diabetes. Secondly, it is desirable to lower homocyst(e)ine levels, since these are highly correlated with coronary heart disease, and homocyst(e)ine is also a recognised risk factor for atherosclerosis. Thus, there is a combined approach, using the homocyst(e)ine strategy together with the diabetes strategy, for controlling vascular disease.

Laugesen and Elliot, 2003 (Laugesen) present further evidence of the link between the consumption of β-casein A¹ and both coronary heart disease and diabetes. In this epidemiology study, Laugesen concludes that the consumption per capita of β-casein A¹ is significantly and positively correlated with ischaemic heart disease in 20 affluent countries. The study also confirms earlier findings made by Elliot that the consumption per capita of β-casein A¹ is correlated with type 1 diabetes mellitus.

A method of producing milk substantially free of β-casein A¹ is described and claimed in the inventor's U.S. patent application Ser. No. 09/906,807. The invention of that application relates to the testing of DNA or RNA from cells obtained from lactating bovines. Those bovines which do not have any DNA or RNA encoding for β-casein A¹ are then selected and milked.

The subject matter of this application relates to the breeding of bovine bulls that do not have DNA encoding for β-casein A¹ with bovine cows that do not have DNA encoding for β-casein A¹. The progeny cows therefore do not produce β-casein A¹ in their milk. These cows are then milked to provide milk suitable for use in the treatment or prevention of coronary heart disease.

It is therefore an object of this invention to provide a method of producing milk substantially free of β-casein A¹ suitable for use in the prevention or treatment of coronary heart disease, or to at least provide a useful alternative.

SUMMARY OF THE INVENTION

In one aspect of the invention there is provided a method of producing milk suitable for use in the treatment or prevention of coronary heart disease from one or more lactating bovines which milk is substantially free of β-casein A¹ but which contains any one or more of β-caseins A², A³, B, C, D and E, the method including the steps of:

(i) breeding one or more bovine bulls that are known to have no DNA encoding for β-casein A¹ with bovine cows which do not have DNA encoding for β-casein A¹ to give progeny which are or includes cows which do not have DNA encoding β-casein A¹; and (ii) milking the progeny cows.

Preferably the method includes the step of testing DNA or RNA from cells containing DNA or RNA obtained from the one or more bovine bulls for the presence of DNA or RNA encoding β-casein A¹.

The method preferably also includes the step of testing DNA or RNA from cells containing DNA or RNA obtained from each of the bovine cows for the presence of DNA or RNA encoding β-casein A¹.

In one alternative, the method may include the step of testing DNA or RNA from cells containing DNA or RNA obtained from the one or more bovine bulls for the presence of DNA or RNA encoding any of β-caseins A¹, B, C and F.

The method may also include the step of testing DNA or RNA from cells containing DNA or RNA obtained from each of the bovine cows for the presence of DNA or RNA encoding any of β-caseins A¹, B, C and F.

In another alternative, the method may include the step of testing DNA or RNA from cells containing DNA or RNA obtained from the one or more bovine bulls for the presence of DNA or RNA encoding β-casein A².

The method may also include the step of testing DNA or RNA from cells containing DNA or RNA obtained from each of the bovine cows for the presence of DNA or RNA encoding β-casein $A^2$.

In a preferred method of the invention the step of testing milk obtained from each of the bovine cows for the presence of β-casein $A^1$ is also included.

The DNA or RNA obtained from the one or more bovine bulls may be obtained from semen, blood, hair, or skin of the one or more bovine bulls. The DNA or RNA obtained from each of the bovine cows may be obtained from blood, hair, or skin of the bovine cows.

The breeding of the one or more bovine bulls with the bovine cows is preferably by artificial insemination, but may alternatively be by natural insemination.

The one or more bovine bulls and the bovine cows are preferably *Bos taurus* bovines.

In a preferred embodiment of the invention the β-casein contained in the milk produced comprises β-casein $A^2$ in the amount greater than 95% by weight of the β-caseins in the milk, more preferably approximately 100% by weight of the β-caseins in the milk.

BRIEF DESCRIPTION OF THE DRAWINGS

FIG. 5 shows the $A^1$ and $A^2$ amplicons for the ACRS genotyping method.

FIG. 7 shows the gene fragment amplified in the Primer Extension genotyping method.

DETAILED DESCRIPTION OF THE INVENTION

Figure 1:
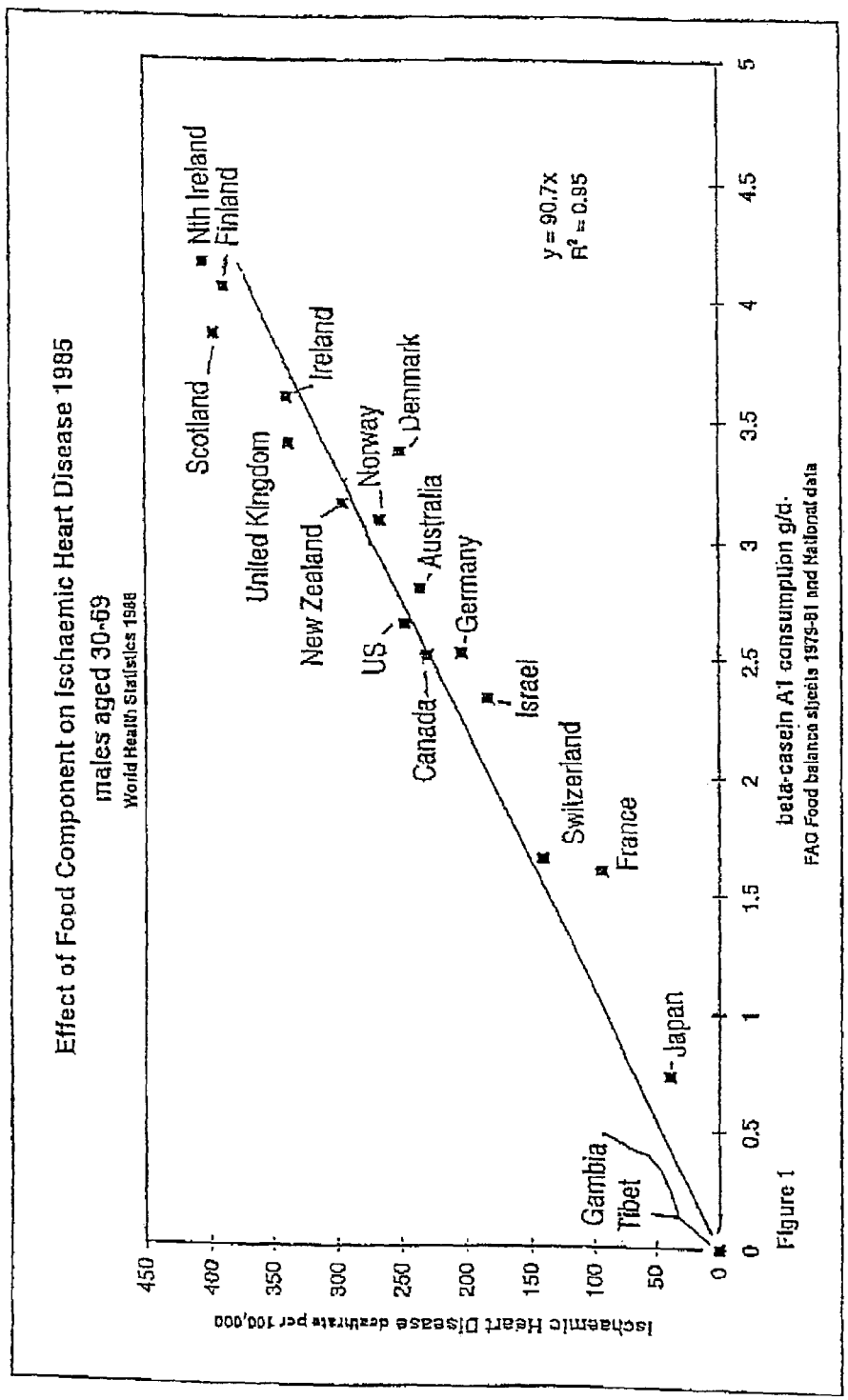
FIG. 1 is a graph showing the regression relationship, between the death rate from Ischaemic heart disease (all ages per 100,000 of population for the year 1985) and the estimated average daily intake of β-casein $A^1$ per head of population (based on country by country dietary information and data on the genotype of the dairy cows in their national herds), over a number of countries.

This invention is applicable to milk, and all products processed from that milk, which milk is substantially free of β-casein $A^1$.

As used herein, the term "treatment" in relation to coronary heart disease means at least a reduction in the risk of a coronary heart disease event occurring in a human. The terms "treat" and "treating" have equivalent meanings.

Coronary heart disease means any disease or disorder relating to the coronary heart system and includes atherosclerosis and ischaemic heart disease.

The term "*Bos taurus*" refers to any cow whose pedigree from its three prior generations is 50% or more of *Bos taurus* origin.

The term "β-casein $A^1$ allele" is a term used with reference to one of the variant forms of the β-casein gene. Expression of the $A^1$ allele results in the production of the β-casein $A^1$ protein. Where reference is made to the presence of the β-casein $A^1$ allele in an individual or population, it encompasses both homozygous and heterozygous genotypes with respect to that allele. Similarly, where reference is made to the presence of β-casein $A^1$, it encompasses phenotypes resulting from either a homozygous or heterozygous state with respect to the β-casein $A^1$ allele.

An example of an animal which is heterozygous for β-casein is a β-casein $A^1A^2$ bovine. Some animals are homozygous, for example bovines that are $A^1A^1$ for β-casein and those that are $A^2A^2$ for β-casein. A β-casein $A^2A^2$ bovine is capable of producing only the β-casein $A^2$ protein.

Genetic variation within a species is due at least in part to differences in the DNA sequence. While there are relatively few such differences in relation to the number of DNA bases or the size of the genome, they can have a major impact as is evident in the genetic heterogeneity of the human and bovine populations. For example, in bovines, a mutation in the DNA sequence coding for the β-casein protein at nucleotide position 200 has resulted in the replacement of a cytidine base with an adenine base. Thus, the triplet codon affected by this change codes for histidine (CAT) rather than for proline (CCT) at amino acid position 67 of the protein. Thus, the histidine at position 67 results in the cow producing β-casein $A^1$ while the proline results in the cow producing β-casein $A^2$ (Note: the preceding discussion assumes that the ancestral bovid expressed β-casein $A^2$ and that there are no other DNA variations at other positions on the DNA sequence).

The term "substantially" as used in the expression "substantially free of β-casein $A^1$" reflects that it cannot be said with 100% certainty that a sample of milk is absolutely free of β-casein $A^1$. On rare occasions, and despite all efforts to ensure that a herd is β-casein $A^1$ free, an animal capable of producing β-casein $A^1$ in its milk could present itself in the herd because of a genetic mutation or because of human error. Herds are formed by the genotype testing of animals and then selecting the desired individuals. All such testing is subject to human error. The phrase "substantially free of β-casein $A^1$" is therefore intended to account for this. Without the word "substantially", the phrase would be unduly limiting.

As used herein, the term "LDL" means low density lipoprotein, "HDL" means high density lipoprotein, and "VLDL" means very low density lipoprotein.

As used herein, the term "triglyceride" means a lipid or neutral fat consisting of glycerol combined with three fatty acid molecules.

As used herein, the term "cardiovascular disease" is any disease of the blood vessels of the circulation system caused by, facilitated by or shown to be linked to abnormally high concentrations of lipids in the vessels.

As used herein the term "arteriosclerosis" is a degeneration of the walls of the arteries due to the formation of foam cells and aortic streaks which narrow the arteries. This limits blood circulation and predisposes an individual to thrombosis.

As used herein, the term "atherosclerosis" is a disease of the arteries in which fatty plaques develop on the inner walls, with eventual obstruction of blood flow.

As used herein, the term "apolipoprotein B" or "apoprotein B" or "Apo B" refers to a specific protein component of plasma lipoproteins involved in lipid and cholesterol transport, most notably LDL and VLDL. Cholesterol synthesised de novo is transported from the liver and intestine to peripheral tissues in the form of lipoproteins. Most of the apolipoprotein B is secreted into the circulatory system associated with VLDL.

As used herein, the term "hypercholesterolemia" means elevated levels of circulating total cholesterol, LDL-cholesterol and VLDL-cholesterol as per the guidelines of the Expert Panel Report of the National Cholesterol Educational Program (NCEP) of Detection, Evaluation of Treatment of High Cholesterol in Adults (Arch. Int. Med. (1988) 148, 36–39).

As used herein, the term "hyperlipidemia" or "hyperlipemia" is a condition where the blood lipid parameters are elevated in the blood. This condition manifests an abnormally high concentration of fats. The lipids fractions in the circulating blood are, total cholesterol, LDLs, VLDLs, and triglycerides.

As used herein, the term "lipoprotein", such as in VLDL, LDL and HDL, refers to a group of proteins found in the serum, plasma and lymph which are important for lipid transport. The chemical composition of each lipoprotein differs in that the HDL has a higher proportion of protein virsus lipid, whereas the VLDL has a lower proportion of protein versus lipid.

As used herein, the term "xanthomatosis" is a disease evidence by a yellowish swelling or plaques in the skin resulting from deposits of fat. The presence of xanthomas are usually accompanied by raised blood cholesterol levels.

As used herein, the term "GRAS" means "generally regarded as safe" with respect to food additives.

The products processed from milk that form part of this invention are derived from a source of bulk milk (i.e. milk from more than one animal) and include, but are not limited to:

(a) bulk milk
(b) bulk milk used to make cheese whether or not the milk has been pasteurised, sterilised or otherwise treated to reduce the the population of microbes prior to cheese making,
(c) milk powders,
(d) milk solids,
(e) caseins, caseinates, and casein hydrolysates,
(f) pasteurised, sterilised, preserved milks including micro-filtered milks, UHT milks,
(g) low fat milks,
(h) modified or enhanced milks,
(i) ice-cream or other frozen dairy based confections,
(j) fermented milk products such as yoghurt or quark,
(k) cheeses including full fat, partial de-fatted and fat-free processed cheeses,
(l) milk whey,
(m) food products enriched through the addition of milk products such as soups,
(n) milk from which potentially allergenic molecules have been removed,
(o) confections such as chocolate,
(p) carbonated milk products, including those with added phosphate and/or citrate,
(q) infant formulations which may contain full, partially de-fatted or nonfat milk together with a number of additional supplements,
(r) liquid or powdered drink mixtures, and
(s) buttermilk and buttermilk powder.

It has been reported that certain human population groups exhibit a relatively low incidence of coronary heart disease and certain other diseases, notwithstanding the fact that they consume considerable quantities of milk and milk proteins. These people include the Tibetans, rural Gambians, and the Masai and Samburu people of Kenya. The inventor has identified the fact that a major difference between these population groups and other similar population groups is that the milk consumed by the above people is derived from *Bos indicus* bovines (e.g. the Zebu breed) and from the Yak (*Bos grunniens*). Such milk does not contain β-casein $A^1$.

In addition, a comparative study in Denmark of the causes of morbidity in the Greenland Eskimo population and the predominant Danes, shows very large relative differences that are suggestive of differences in life-style risk factors. One notable difference is that the Danes are large consumers of dairy products whereas the Eskimos are not. The differences in morbidity are illustrated in Table 1 below.

TABLE 1

Age-adjusted differences in morbidity from chronic diseases between Greenland Eskimos and Danes

| | Eskimos/Danes |
|---|---|
| Acute myocardial infarction | 1/10 |
| Stroke | 2/1 |
| Psoriasis | 1/20 |
| Diabetes | Rare |
| Bronchial asthma | 1/25 |
| Malignant disorders | 1/1 |
| Thyrotoxicosis | rare |
| Multiple sclerosis | 0 |
| Polyarthritis chronica | Low |

Acta Med. Scand., 208:401–406, (1980)

A further comparison has been carried out using data from the states of the former West Germany. In this case, the coronary heart disease death rates have been found to correlate strongly with the relative regional average consumption of β-casein $A^1$ (Table 2). In this instance, the composition of the individual state dairy herds remained virtually constant from the 1950's through to the 1980's.

The data show a remarkable relationship between the relative incidence of Ischaemic heart disease and the relative average consumption of β-casein $A^1$ across the 8 states. This is in marked contrast to the relatively poor relationships between the incidence of Ischaemic heart disease and the recognised listed dietary risk factors.

TABLE 2

A comparison of the relative nutritional risk factors for coronary heart disease and the incidence of Ischaemic heart disease (IHD) in the states of the former Federal Republic of Germany (Schleswig-Holstein = 1.00)

| | Relative intake of dietary component | | | | | | Relative incidence of IHD |
|---|---|---|---|---|---|---|---|
| | Saturated Fat | Cholesterol | Alcohol | Carbohydrates | Energy | β-casein $A^1$ | |
| Schleswig Holstein | 1.00 | 1.00 | 1.00 | 1.00 | 1.00 | 1.00 | 1.00 |
| Niedersachsen | 0.97 | 0.96 | 1.00 | 0.98 | 0.99 | 0.92 | 0.88 |
| Nordrhein Westfalen | 0.99 | 1.02 | 0.99 | 1.00 | 1.02 | 0.97 | 1.00 |
| Hessen | 0.95 | 0.96 | 0.98 | 0.98 | 0.98 | 0.75 | 0.74 |
| Rheinland-Pfalz | 0.95 | 0.99 | 1.00 | 1.02 | 1.0 | 0.87 | 0.78 |
| Saarland | 0.94 | 0.93 | 0.98 | 1.01 | 0.98 | 0.90 | 0.88 |
| Baden Wurttenburg | 0.93 | 1.02 | 1.02 | 1.05 | 1.03 | 0.50 | 0.72 |
| Bayern | 0.96 | 0.99 | 1.22 | 1.06 | 1.02 | 0.50 | 0.74 |

A regression relationship between ischaemic heart disease and fat intake was conducted and was shown to be not significant ($p<0.0684$, $r^2=0.20$). However, the regression between ischaemic heart disease and the intake of β-casein $A^1$ was highly significant ($p<0.0001$, $r^2=0.71$). The regression relationships are:

$$IHD=1.56(\pm 0.79)\text{Fat Intake}+86.7(\pm 74.9)$$

$$IHD=81.7(\pm 13.5)\beta\text{-Casein } A^1-5.4(\pm 40.4)$$

The multiple regression relationship was then generated. In this case, the inclusion of both fat intake and β-casein $A^1$ intake did not improve the relationship over that with β-casein $A^1$ alone. The regression relationship is:

$$IHD=78.3(\pm 15.6)\beta\text{-Casein } A^1+0.259(\pm 0.557)\text{Fat}-19.2(\pm 51.0)$$

The analyses of the relationships between various dietary factors and ischaemic heart disease outlined in this document indicate the potential importance of the β-casein variant as a risk factor for heart disease. The difference between the two casein variants is only one amino acid. This suggests that the products of proteolysis of these variants may be linked to the identified risk factor. Some indication of the number, and the major product fragments into which they are split by proteolytic action of a variety of enzymes, is illustrated for the β-caseins in Table 3.

TABLE 3

The β-casein family of proteins

| Former Nomenclature | Recommended Nomenclature | Source of Fragment |
|---|---|---|
| β-casein $A^1$ | β-CN $A^1$-5P | — |
| β-casein $A^2$ | β-CN $A^2$-5P | — |
| β-casein $A^3$ | β-CN $A^3$-5P | — |
| β-casein B | β-CN B-5P | — |
| β-casein D | β-CN C-4P | — |
| β-casein D | β-CN D-4P | — |
| β-casein E | β-CN E-5P | — |
| $\gamma_1$-casein $A^1$ | β-CN $A^1$-1P(f29–209) | β-CN $A^1$-5P |
| $\gamma_1$-casein $A^2$ | β-CN $A^2$-1P(f29–209) | β-CN $A^2$-5P |
| $\gamma_1$-casein $A^3$ | β-CN $A^3$-1P(f29–209) | β-CN $A^3$-5P |
| $\gamma_1$-casein B | β-CN B-1P(f29–209) | β-CN B-5P |
| $\gamma_2$-casein $A^2$ | β-CN $A^2$ (f106–209) | β-CN $A^1$-5P or β-CN $A^2$-5P |
| $\gamma_2$-casein $A^3$ | β-CN $A^3$ (f106–209) | β-CN $A^3$-5P |
| $\gamma_2$-casein B | β-CN B (f106–209) | β-CN B-5P |
| $\gamma_3$-casein A | β-CN A (f108–209) | β-CN $A^1$-5P, β-CN $A^2$-5P or β-CN $A^3$-5P |
| $\gamma_3$-casein B | β-CN B (f108–209) | β-CN B |

In addition there are a number of protease peptone components.
Eigel, 1984 (Eigel)

Bovine milk is an important source of proteins and other nutrients required by humans. A high proportion of the common domestic cattle breeds, such as the Holstein, express the β-casein $A^1$ allele. For example, it is estimated that in the late 1980s more than 70% of the Californian dairy herd carried the $A^1$ allele. As noted previously, the β-casein $A^1$ variant is of particular interest and therefore, considering its contribution to milk consumed by the human population in many parts of the world, the proteolysis products of β-casein $A^1$ are of particular interest.

Figure 3:
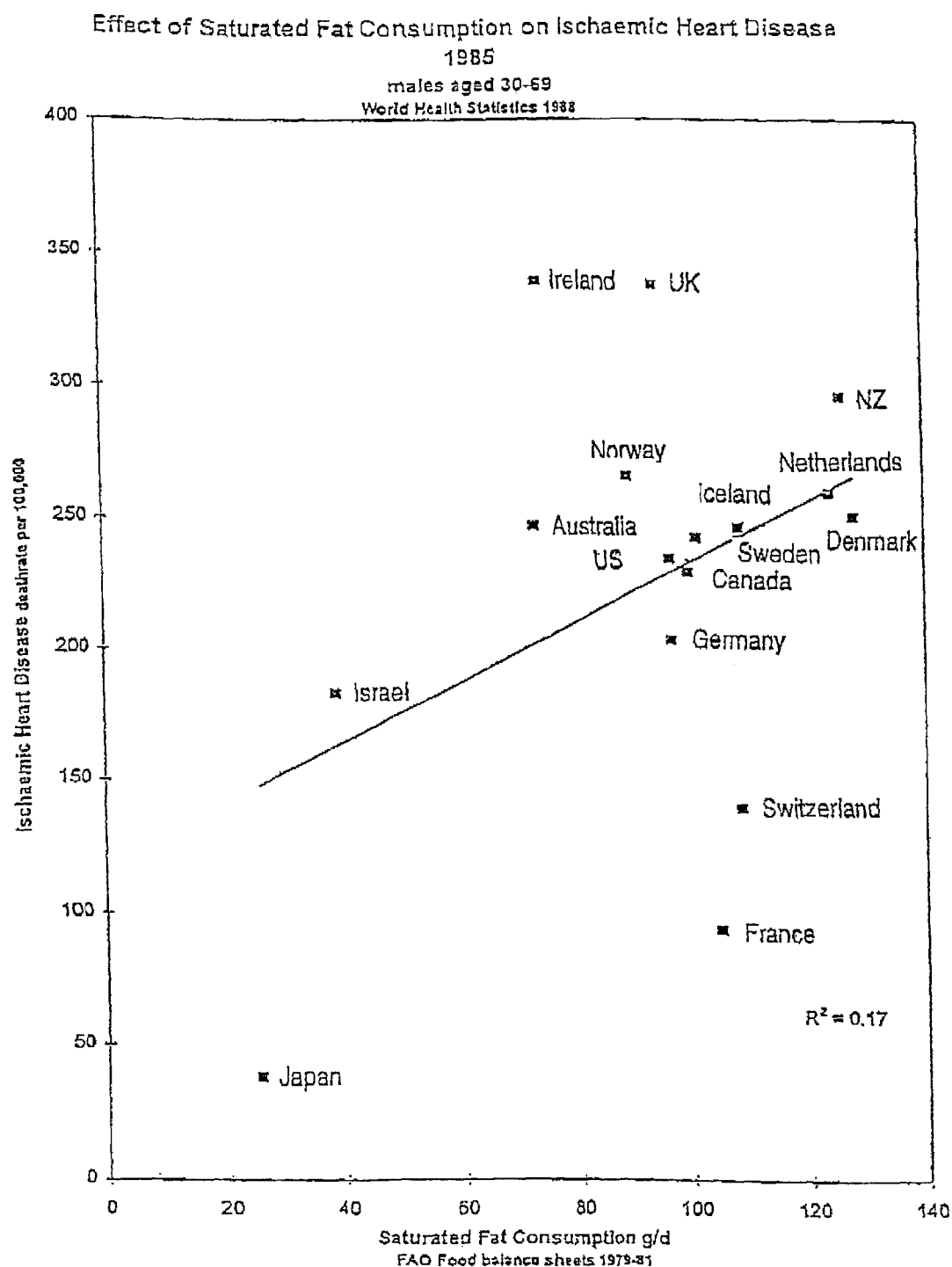
FIG. 3 is a graph showing the regression relationship between the death rate from Ischaemic heart disease (per 100,000 males aged 30–69 for the year 1985) and the estimated average daily intake of saturated fat over a number of countries.
Figure 4:
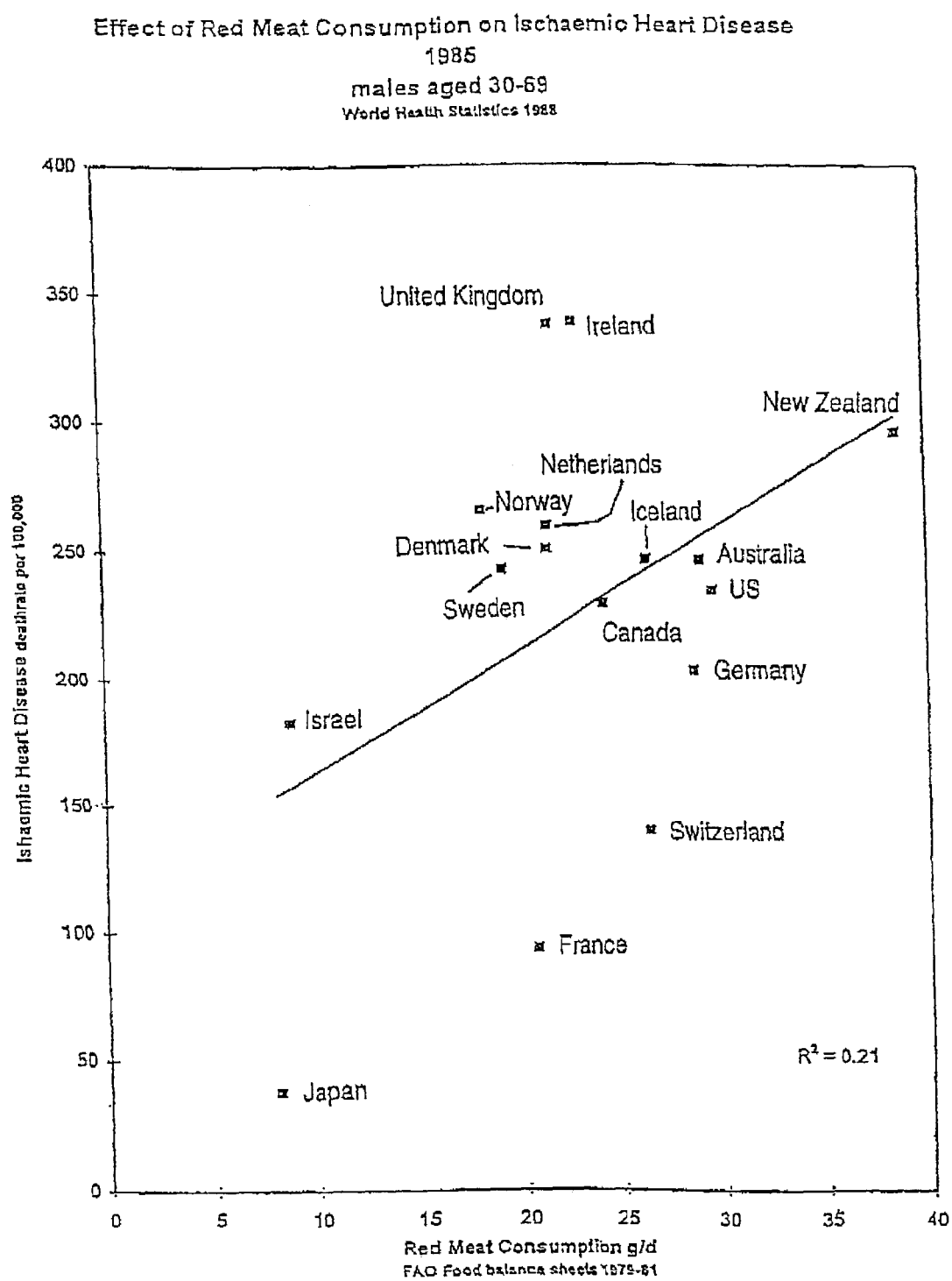
FIG. 4 is a graph showing the regression relationship between the death rate from Ischaemic heart disease (per 100,000 males aged 30–69 for the year 1985) and the estimated average daily intake of red meat over a number of countries.

In the graph shown in FIG. 1, the incidence of Ischaemic heart disease is plotted against the estimated average consumption of β-casein $A^1$ (and its derived proteolysis products). FIG. 1 shows a very strong correlation between the consumption of β-casein $A^1$ and death rate from Ischaemic heart disease. In contrast, the correlation with the consumption of dairy protein (FIG. 2) is much lower. Neither saturated fat consumption (FIG. 3) nor the consumption of red meat (FIG. 4) show the strong correlation which the inventor has identified in relation to the consumption of β-casein $A^1$, both between countries and within countries.

The single amino acid difference between the two predominant β-casein variants has highlighted the potential role of a difference in the proteolysis products from different β-casein variants as potential risk factors for coronary heart disease. Therefore, the potential impact of pasteurisation is of interest, as prolonged heating is a factor that is known to influence proteolysis and the monomer to micelle ratio which is known to affect digestion of β-casein. In particular, this relates to the more severe forms of heat treatment that were used in the early years of pasteurisation (e.g. Holder pasteurisation which heats milk to 63° C. and holds it for 20–30 minutes). Hence the impact of the introduction of Holder pasteurisation on the death rate from coronary heart disease is of interest. The inventor has examined the available data and the results of the analyses are presented in Table 4.

The analyses reveal a very marked and sudden increase in the death rate from coronary heart disease in the four years after the introduction of Holder pasteurisation. Such data would suggest the presence of a novel risk factor associated with pasteurisation. It is the inventor's contention that this risk factor may be associated with a derivative of β-casein $A^1$ (for example, a proteolysis product).

TABLE 4

Comparison of the death rates due to coronary heart disease before and after the introduction of Holder Pasteurisation in different parts of the UK

| Population group | Holder intro. year | Angina pectoris (AP1) mort. per mill. | | | | Cerebral embolism and thrombosis (CET) | | | |
|---|---|---|---|---|---|---|---|---|---|
| | | AP1 | AP2 | AP3 | Δ% | CET1 | CEL2 | CET3 | Δ% |
| U.K. | | | | | | | | | |
| Edinburgy | 1923 | 1925 | 67 | 92 | 37[a] | 1924 | 174 | 236 | 36 |
| Glasgow | 1924 | 1924 | 56 | 91 | 62[a] | 1924 | 77 | 101 | 31 |
| Dundee | 1924 | 1925 | 42 | 64 | 52[a] | 1925 | 162 | 188 | 16 |
| Aberdeen | 1926 | 1926 | 91 | 135 | 48[a] | 1927 | 121 | 227 | 88 |
| Lanarkshire (excluding Glasglow) | 1935 | 1937 | 188 | 375 | 99[b] | 1938 | 153 | 193 | 26 |
| | 1947 | 1948 | 685 | 1185 | 73 | 1948 | 298 | 518 | 74 |
| | 1952 | 1954 | 1185 | 1523 | 29 | 1954 | 518 | 680 | 31 |
| Country of Sutherland | 1954 | 1954 | 963 | 1710 | 78 | 1954 | 610 | 823 | 35 |
| Country of Bute | 1956 | 1956 | 1610 | 2848 | 78 | 1956 | 955 | 1398 | 46 |
| London Admin. County | 1925 | 1925 | 31 | 112 | 261[c] | 1926 | 90 | 120 | 33 |
| Average increase | | | | | 82 | | | | 42 |
| Norway | | | | | | | | | |
| Oslo | 1922 | 1922 | 3 | 43 | 1333.3[d] | not available | | | |

Annand, 1967 (Annand)
Columns AP1 and CET1 denote the year of commencement of the sudden rise in the appropriate mortality.
Columns AP2 and CET2 denote the appropriate average mortality for the 4 years immediately preceeding the year of introduction.
Columns AP3 and CET3 denote the appropriate average mortality for the 4 years immediately succeeding the introduction of pasteurisation.
Δ% represents average increase.
[a]Possibly low because deaths ascribed to "coronary thrombosis" were not included in International List No. 89 in Scotland until 1931.
[b]Possibly high as deaths ascribed to "coronary thrombosis" were included in International List No. 94.
[c]Possibly high because after 1927 all deaths ascribed to "coronary thrombosis" were included (unlike those in Scotland) in International List No. 89.
[d]Mortality ascribed to the following classification groups: angina pectoris, infarctus cordis, sclerosis art. coron. Cordis.

It is possible, however, that a specific fragment or fragments of β-casein $A^1$ affect the body's immune system as a result of their immunosuppressant properties. By reducing or substantially eliminating the presence of β-casein $A^1$ in the diet of an individual, it is believed that its immune response may be enhanced, or immunosuppression reduced, thereby improving the general well-being of the individual. It is believed that some individuals may be particularly susceptible to the presence of β-casein $A^1$, and it may be possible to develop a test for such susceptible individuals, and to recommend that they reduce or eliminate the consumption of milk or other dairy products containing β-casein A$^1$.

In humans, low density lipoprotein (LDL) oxidation is considered to be a primary step in the evolution of artherosclerotic damage (Steinberg et. al., 1989). Analysis of protein oxidation products isolated from atherosclerotic lesions implicates the tyrosyl radical (a reactive nitrogen species) and hypochlorous acid in LDL oxidation (Heinecke et. al., 1999). In addition, it has been found (Torreilles and Guerin, 1995) that β-casomorphin-7 (and truncated forms, e.g. β-casomorphins 5 and 6) could promote peroxidase-dependent oxidation of human LDLs. The reaction is independent of free metal ions but requires casein-derived peptides with tyrosyl end residues. This implies that the tyrosyl ending peptide is a diffusable catalyst that conveys oxidising potential from the active site of the heme enzyme to LDL lipids. Casomorphin-7 is a potential source of a tyrosyl radical and has been shown to cause LDL peroxidation. Casomorphin-7 is produced from β-casein A$^1$, but not from β-casein A$^2$ (Jinsmaa et. al., 1999).

Hypercholesterolemia is a condition with elevated levels of circulating total cholesterol, (low density lipoprotein) LDL-cholesterol and (very low density lipoprotein) VLDL-cholesterol. In particular, high levels of LDL and VLDL are positively associated with coronary arteriosclerosis while high levels of HDL are negative risk factors. The role of LDL oxidation has gained much attention in the literature. It is well documented that modified LDL, or more specifically oxidised LDL, has an increased ability to bind endothelial and smooth muscle cell walls thus promoting further injury by continued oxidation within the lumen of arteries.

Furthermore, oxidised LDL is known to invoke a range of physiological responses directly involved in the atherosclerotic process. These responses include the stimulation of the secretion of mediators of inflammatory response (e.g. interleukin-1, interleukin-6, tumour necrosis factor alpha and macrophage colony stimulating factor) which are chemoattractants for macrophages which recognise the oxidised LDL within the subendothelial space and actively engulf them, subsequently turning into foam cells. The foam cells then aggregate to form fatty streaks. Such fatty streaks are the first identifiable characteristic lesion of advanced atherosclerosis.

Hyperlipidemia also predisposes one to coronary heart disease, as well as to cancer and obesity. Hyperlipidemia is one of the high risk factors useful in the early diagnosis of these life threatening diseases.

Hyperlipidemia is a condition where the blood lipid parameters are elevated. The lipids fractions in the circulating blood are total cholesterol, LDL, VLDL, and triglycerides. Safe levels of these according to the American Heart Association guidelines are represented below. Active treatment by diet modifications and drugs are necessary to reduce the risk of fatality when the levels are abnormal.

| Total Cholesterol | (TC) > 240 mg/dL |
|---|---|
| LDL-Cholesterol | >160 mg/dL - Apo(B) Atherogenic factor |
| HDL-Cholesterol | <35 mg/dL Lp(a) Atherogenic factor |
| Triglycerides | >150 mg/dL |

As with hypercholesterolemia, hyperlipidemia results from diet, heredity, lifestyle, environment, familial diseases, or stress. The condition may be inherited or may be secondary to another disorder, such as systemic lupus erythematosus (SLE), hypothyroidism, nephrotic syndrome, Cushing's syndrome, diabetes mellitus, obesity, alcoholism, corticosteroid therapy or estrogen therapy.

Hypercholesterolemia and hyperlipidemia are also major causes of atherosclerosis. Atherosclerosis is responsible for more deaths in the U.S. than any other single condition. Atherosclerotic heart disease involving the coronary arteries is the most common single cause of death, accounting for one third of all deaths. Atherosclerotic interference with blood supply to the brain (causing stroke) is the third most common cause of death (after cancer). Atherosclerosis also causes a great deal of serious illness by reducing the blood flow in other major arteries, such as those to the kidneys, the legs and the intestines.

Atherosclerosis is a cardiovascular condition that occurs as a result of narrowing down, or stenosis, of the arterial walls. The narrowing is due to the formation of plaques (raised patches) or streaks in the inner lining of the arteries. These plaques consist of oxidised-LDL, monocytes, macrophages, foam cells, damaged muscle cells, fibrous tissue, clumps of blood platelets, cholesterol, and sometimes calcium. They tend to form in regions of turbulent blood flow and are found most often in people with high concentrations of cholesterol in the bloodstream. The number and thickness of plaques increases with age, causing loss of the smooth lining of the blood vessels and encouraging the formation of thrombi (blood clots). It is not uncommon for fragments of thrombi to break off and form emboli, which travel through the bloodstream and block smaller vessels (e.g. coronary arteries) leading to ischaemic damage of tissue, or ischaemic heart disease.

Medication is not a satisfactory treatment for ischaemic heart disease because much of the damage to the artery walls has already been done. Anticoagulant drugs have been used to try to minimise secondary clotting and embolus formation, but these have little or no effect on the progress of the disease. Vasodilator drugs are used to provide symptom relief, but are of no curative value.

Surgical treatment is available for certain high-risk situations. Balloon angioplasty can open up narrowed vessels and promote an unproved blood supply. The blood supply to the heart muscle, following coronary vessel blockage or damage, can also be restored through a vein graft bypass. Large atheromas and calcified arterial obstructions can be removed by endarterectomy, and entire segments of diseased peripheral vessels can be replaced by woven plastic tube grafts.

In some instances the reduction of hypercholesterolemia can be achieved by modification of the diet and/or use of drugs thereby minimizing the risk of fatality from the disease. Reduction of serum cholesterol in humans has been achieved by consumption of dietary plant fibre and other effective components of foods. However, there remains a need for a safe and effective treatment for the above conditions.

The inventors have surprisingly found that consumption of β-casein A$^2$ reduces serum cholesterol levels, reduces circulating triglyceride levels, reduces LDL concentrations and thus LDL:HDL ratios, reduces serum levels of apolipoprotein B and is atheroprotective.

These effects observed by the inventors mean that the consumption of β-casein A$^2$ is beneficial for the prevention or treatment of a variety of diseases or disorders including hypercholesterolemia, hyperlipidemia, and atherosclerosis. The finding is supported by experimental studies where ten groups of NZ white rabbits were fed ad libitum with controlled diets (see Example 3).

Recognising that dairy products free from β-casein A¹ are desirable, it is preferable to ensure that the animal from which the product is derived has been tested for the presence of the β-casein A¹ allele. Subsequent separation of the bovines into separate herds and/or selective breeding programmes (selecting for β-casein A¹ negative animals) can be carried out to eliminate the presence of the β-casein A¹ from the herd.

While the subject of U.S. patent application Ser. No. 09/906,807 is the selection of bovine cows for milking based on genotyping of the cows for the presence of DNA or RNA encoding β-casein A¹, or other β-caseins, this invention is directed to the breeding of cows with bulls to give progeny cows that produce milk free of the β-casein A¹ protein.

If both parents of a cow are known to have no DNA encoding for β-casein A¹, then the cow will not have the ability to produce β-casein A¹ in its milk. Determination of whether the parents have DNA encoding for β-casein A¹ may be by a variety of methods. One method is by genotyping a bull and breeding it with a cow known to have no DNA encoding for β-casein A¹. An alternative method is by genotyping a cow and breeding it with a bull known to have no DNA encoding for β-casein A¹.

A preferred method of the invention is the genotyping of a bovine bull to establish that it has no DNA encoding for β-casein A¹ and then breeding that bull with bovine cows known (by genotyping or any other method) to have no DNA encoding for β-casein A¹. The progeny cows can then milked to give milk that is free of β-casein A¹. Preferably the milk contains only β-casein A² of the possible β-casein variants.

The breeding may be by natural or artificial insemination. Artificial insemination is anticipated to be the prevalent method.

Any known method for the genotyping of bovines may be used. Such methods can be specific for DNA or RNA encoding either β-casein A¹ or β-casein A². However, general methods which do not specifically test for DNA or RNA encoding β-casein A¹, but additionally test for DNA or RNA encoding other β-caseins, may also be used to form a herd of bovines which do not produce β-casein A¹ or produce only β-casein A² of the possible β-casein variants in their milk.

For the avoidance of any doubt, any reference to DNA in the methodology of this invention is intended to include cDNA (which is DNA derived from RNA).

For example, it is known that β-casein A¹ has histidine at position 67 of the protein whereas β-casein A² has proline at the same position. This is due to the presence of an adenine nucleotide at position 200 of the β-casein DNA. This produces the triplet codon that specifies histidine (CAT) rather than proline (CCT). A test which identifies the codon that will specify histidine at position 67 of the β-casein protein can therefore be used to exclude bovines which produce β-casein A¹ in their milk.

Similarly, a test which identifies the codon that will specify proline at position 67 of the β-casein protein can therefore be used to select bovines which produce β-casein A² (or β-caseins A³, D or E) in their milk. While a test for animals that are homozygous for the presence of CCT (that codes for proline) at codon 67 of an animal's β-casein gene does not unequivically show whether or not the animal is homozygous for the β-casein A² allele, the test can show that an animal does not possess any of the alleles for β-casein A¹, B and C. Such a test does not need to be any more specific because culling animals negative for the test will mean the elimination of β-casein A¹ producing animals from the herd.

It is also known that β-caseins B, C and F, in addition to β-casein A¹, have histidine at position 67. Also, β-caseins A³, D and E, in addition to β-casein A², have proline at position 67. Therefore, a test which distinguishes between the codons that specify proline and histidine at position 67 will also distinguish between β-caseins A¹, B, C and F on the one hand and β-caseins A², A³, D and E on the other hand.

For example, while a test for the presence of CAT (histidine) or absence of CCT (proline) in one or other or both of an animal's alleles at codon 67 of its β-casein gene does not unequivocally show whether or not the animal contains the β-casein A¹ allele, the test can show that an animal may contain one or more of the alleles for β-casein A¹, B, C and F. Such a test does not need to be any more specific because culling animals positive for the test (i.e. absence of the proline codon in at least one allele) will mean the elimination of β-casein A¹ producing animals from the herd.

A DNA or RNA test which gives positive identification for animals homozygous for CCT (proline) at codon 67 can therefore be used to ascertain whether a particular bovine does not possess a β-casein A¹ allele, whether homozygous or heterozygous. Thus, bovines which do possess the CCT (proline) at codon 67 at one or both alleles can therefore be culled from a herd to give a herd which is free of the β-casein A¹ allele. Milk obtained from that herd therefore cannot contain β-casein A¹.

Where it is known that the genetic makeup of the herd is such that the only possible alleles possessed by the individuals are for β-caseins A¹ and A², the culling from the herd of those bovines positive for histidine at position 67 gives a herd where each individual is homozygous for the β-casein A² allele. Such a herd will produce milk possessing only β-casein A².

The determination of whether the genotype at codon 67 of the β-casein gene is CCT (proline) or CAT (histidine) can be made by many different methods that are available and which could be used to assay for this single nucleotide polymorphism (SNP). The methods include DNA sequencing, SSCP (single stranded conformation polymorphism), allele specific amplification, and assays designed using proprietary chemistries such as Taqman™ (PE Biosystems), Invader™ (Third Wave Technologies), SnapShot™ (PE Biosystems), Pyrosequencing™ (Pyrosequencing AB), Sniper™ (Pharmacia), and DNA chips (hybridisation or primer extension chips).

The preferred method should have the ability to function well with rapidly extracted impure DNA. High test throughput (>1000 of samples per day) at low cost is desirable. Since the preferred objective is to identify bovines that are homozygous for the β-casein A² allele, the unequivocal positive identification of animals homozygous for CCT at codon 67 is preferred, rather than simply the absence of a result in a test for the alternative CAT codon.

Two examples of practical methods for the large scale genotyping of bovines are:

A manual ACRS (amplification created restriction site) method which can be conducted easily in any molecular genetics laboratory and requires no specialist equipment or devices. The method can be easily scaled up to analyse hundreds of samples per day.

A highly automated method such as the Sequenom™ primer extension and mass spectrometry system which is capable of analysing thousands of samples per day.

The aim of the ACRS method is to create an amplicon in which only one allele of an SNP will form a restriction site. The restriction site is created by site directed mutagenesis in the amplification step.

A Dde1 restriction site can be created when the nucleotides CT are present at nucleotide 200 and 201 (positions 2 and 3 of codon 67) of the β-casein gene. This would positively identify the presence of the CCT (proline) codon.

In Example 1 below, the 3' section of the Casein Dde2 primer has a mismatch at its penultimate nucleotide (FIG. 5). This is important as it creates a Dde1 restriction site in the $A^2$ amplicon only (shown in italics in FIG. 5). In FIG. 5, codon 67 in each template is in bold lowercase. The template is reversed to present the primer in the usual 5'–3' orientation. The mismatch base is underlined.

Variations of the test could include modification of the sequence of the 5' end of the Casein Dde2 primer or 5' extension of the Casein Dde2 primer with a nucleotide sequence homologous to the β-casein template or 5' extension of the Casein Dde2 primer with nucleotides which are not homologous to the β-casein sequence. The second primer for the ACRS is less critical and many compatible primers could be used. The primer known as Casein4 5'-CCTTCTTTCCAGGATGAACTCCAGG-3' (SEQ ID NO: 2) has been found to be the most effective.

PCR amplification with this pair of primers produces a 121 base pair fragment in all β-casein alleles. However, the definitive diagnostic step is that only alleles with CT at positions 200 and 201 (i.e. specifying amino acid 67 of the β-casein) can be cut with the restriction enzyme Dde1. This produces distinctive 86- and 35- base pair fragments.

The first step of the primer extension method is PCR amplification of the region of the β-casein gene containing codon 67. In Example 2 below, a 319 bp fragment (shown in FIG. 7), was amplified. In FIG. 7, the primer regions are shown underlined. Alternate bases of the SNP are shown bracketed.

The post PCR product is cleaned with a SAP reaction to remove unincorporated dNTPs. An extension primer complementary to the bold itallicised sequence is added to the cleaned product along with an extension mixture containing ddA, ddC, ddT and dG. The following size extension products are obtained:

separately. Ideally the milk from that separate herd is kept separate from other milk which may contain β-casein $A^1$.

The selected bovines may be uniquely identified (e.g. alternatives include ear-tagging with a unique tag, or use of an electronic tag or use of a specific tag that identifies the bovine as being free of the β-casein $A^1$ allele or branding for future identification). The selected bovines are milked to give milk free of β-casein $A^1$. Preferably, the milk is phenotype tested to confirm that the milk is substantially free of β-casein $A^1$.

A bulk quantity of milk from the selected bovines may then be processed into one or more milk products, such as fresh milk, cheeses, yoghurts, milk powders etc.

With the objective of investigating any positive effects of the consumption of β-casein $A^2$, rather than the positive effects of avoiding β-casein $A^1$, rabbit feeding studies were undertaken and are described in Example 3. The results were found to be consistent with the epidemiology studies described above and, further, indicate that the consumption of β-casein $A^2$ is beneficial.

In rabbit Groups 3–8, three concentrations of β-casein $A^1$ and $A^2$ (5%, 10% and 20%) in the diet were tested, with whey protein added such that a total of 20% milk protein was present in each diet (i.e. 15%, 10%, 0% added whey protein respectively). Cholesterol (0.5%) was also added to these diets to ensure measurable lesions. As controls, Group 1 rabbits were fed 20% whey protein and Group 2 rabbits were fed 20% whey protein plus 0.5% cholesterol. Groups 9 and 10 were fed 10% β-casein $A^1$ (or $A^2$) plus 10% whey only. The rabbits on the specially prepared diet ate only an average of 30.05±0.97 grams per day.

Not surprisingly, almost all rabbits lost weight over the 6 week experimental period, with a 5.62% average weight loss. This did not affect their overall health and the rabbits were alert, responsive and showed no signs of distress. This is consistent with an earlier study which found that, with rabbits fed a semisynthetic diet containing casein, the feed intake and weight gain was reduced by half as the diet was not readily accepted, although the rabbits still appeared healthy. Rabbits placed on a high level of dietary casein (50%) failed to gain weight during the course of that study.

10% β-Casein $A^2$ with no added cholesterol (Group 10) produced a significantly lower serum cholesterol level at t=6

| Name | Mass (Da) | Sequence (5'—3') | SEQ ID NO: |
|---|---|---|---|
| Primer AGR-RMA6 | 5920.90 | GTTTTGTGGGAGGCTGTTA | 3 |
| Contaminant (Pause) | 6250.10 | GTTTTGTGGGAGGCTGTTAG | 4 |
| Analyte A | 6209.10 | GTTTTGTGGGAGGCTGTTAT | 5 |
| Analyte C | 7205.70 | GTTTTGTGGGAGGCTGTTAGGGA | 6 |

If codon 67 of β-casein is CAT, a 20 bp, 6209.10 Dalton product is obtained, whereas if the sequence is CCT, a 23 bp, 7205.70 Dalton product is obtained. These products can be clearly distinguished and separated from possible contaminants by MALDI-TOF mass spectrometry.

The results of the genotype testing obtained from either method are then used to select bovines positively identified as having CCT (proline) at position 67 at both alleles. Such bovines cannot produce β-casein $A^1$ in their milk. The selected bovines are kept in a separate herd and are milked weeks than all other Groups including whey only (Group 1) and 10% β-casein $A^1$ (Group 9). The β-casein $A^1$ Group had serum cholesterol levels higher than the whey only Group. This highlights the necessity to examine the effect of the specific β-caseins rather than mixtures, and is the first time that the differential effects of β-casein variants on serum cholesterol levels have been described.

The mean serum cholesterol level in rabbits fed 20% β-casein $A^1$ alone (Group 9) was higher than those in Group 1 (whey only) animals. Thus, β-casein $A^1$ may be slightly more atherogenic than whey protein. Adding 0.5% cholesterol to all diets increased the serum cholesterol levels at least 3-fold, which was much greater than the effect of $A^1$ β-casein compared with whey alone. There was no significant difference between the serum cholesterol levels of rabbits fed β-casein $A^1$ or $A^2$ in the presence of added dietary cholesterol.

The level of serum LDL in Group 10 (β-casein $A^2$) was significantly lower than that in Groups 9 (β-casein $A^1$) or 1 (whey only), all with no dietary cholesterol. The level of LDL for Group 9 was higher than that for Group 1, but not significantly. In the presence of added dietary cholesterol, serum LDL was significantly elevated in all Groups (2–8) and these were not significantly different from each other. A similar pattern occurred for serum HDL except that Group 10 was not significantly lower than Group 1.

The anti-atherogenic potential of β-casein $A^2$ was further highlighted by the ratios of LDL to HDL. There was a much greater difference in serum LDL levels between Groups 9 (β-casein $A^1$) and 10 (β-casein $A^2$) than in serum HDL levels. Thus the LDL to HDL ratios were significantly less for β-casein $A^2$ fed animals than for β-casein $A^1$ fed animals. Indeed, the LDL to HDL ratio of Group 10 was significantly lower than all other groups, including Group 1 (20% whey alone). There was no significant difference between all groups for triglycerides or homocysteine.

Thus, dietary β-casein $A^2$, in the absence of a cholesterol-enriched diet, leads to lower serum cholesterol levels (total, LDL and HDL) than both β-casein $A^1$ and whey.

It was found that both β-casein $A^1$ and $A^2$ led to fatty streaks compared with 20% whey, but β-casein $A^2$ produced less extensive lesions than β-casein $A^1$. Indeed, 10% β-casein $A^1$ without dietary cholesterol produced about the same amount of lesions as 10% β-casein $A^2$ with added dietary cholesterol. The thickness of fatty streaks in the aortic arch of rabbits fed β-casein $A^2$, either with or without dietary cholesterol, was zero or else very close to zero. In contrast, the thickness of aortic arch fatty streaks in rabbits fed β-casein $A^1$ was significantly higher. Thus, β-casein $A^1$ is more atherogenic than both whey and the $A^2$ casein variant.

In the presence of 0.5% dietary cholesterol, only 20% β-casein $A^2$ produced a smaller surface area of aorta covered by fatty streaks than 20% whey. However, the thickness of the fatty streaks in the aortic arch was significantly smaller for both 20% and 5% □-casein $A^2$-fed animals compared with whey (0.03±0.015), with a low (but not significant) value for 10% β-casein $A^2$ fed animals (0.01±0.008).

Balloon injury of arteries combined with a cholesterol-enriched diet is known to produce lesions in rabbits that closely resemble advanced human atheroma.

There was no significant difference in intima to media ratio of the balloon injured right carotid artery of rabbits fed β-casein $A^1$ or $A^2$ either with or without dietary cholesterol. However, groups fed β-casein $A^2$ (both with and without added cholesterol) had smaller neointimal thickenings than their β-casein $A^1$ fed counterparts. Animals fed β-casein $A^2$ generally had slightly thinner intimas than those fed whey (both with and without dietary cholesterol).

These results, combined with the fact that 10% $A^2$ with no added cholesterol produced a significantly lower serum cholesterol level than all other groups including whey only and 10% β-casein $A^1$, demonstrate for the first time that β-casein $A^2$ has an atheroprotective effect while β-casein $A^1$ is atherogenic.

The invention is further described with reference to the following examples. However, it is to be appreciated that the invention is not limited to the examples.

EXAMPLES

Example 1

ACRS Method

At least 10 hairs were pulled from the end of the tail switch of a cow so that the hook-shaped follicles were retained on the end of the removed hairs. This was achieved easily by pulling the tail hairs upward while holding the rest of the switch down. If the tail has been docked, longer hairs from the end of the docked tail or other locations on the body may be substituted. Tail hairs are preferred.

Five hair follicles from one cow were cut into a sterile 1.5 ml microfuge tube. Solution A (200 µl) was added to the tube and the tube placed in a boiling water bath for 15 minutes. The tube was removed and Solution B (200 µl) added followed by mixing.

Solution A (200 mM NaOH)

Solution B (100 mM Tris-HCl, pH 8.5 with an extra 200 mM HCl)—prepared by combining 1 M Tris-HCl, pH 8.5 (10 ml) with conc. HCl (1.67 ml) and making up to 100 ml with distilled water.

Crude DNA extract (1.5 µl) from hair follicles (prepared as above) or DNA (20–50 ng) (prepared by another method) was transferred to a well of a 96-well PCR plate. PCR cocktail (20 µl) was added to the well. The well was overlayed with mineral oil and centrifuged briefly to remove air bubbles.

The PCR cocktail was prepared according to the following:

| Components | Final Concentration |
| --- | --- |
| 10X PCR Buffer minus Mg (GibcoBRL ®): | 20 mM Tris-HCl (pH 8.4), 50 mM KCl |
| 2 mM dNTPs mixture (GibcoBRL ®): | 0.2 mM each |
| 50 mM $MgCl_2$ (GibcoBRL ®): | 1.3 mM |
| Primers: 20 µM Casein4 | 0.5 µM |
| 20 µM CaseinDde2 | 0.5 µM |
| Taq DNA Polymerase 5 U/µl (GibcoBRL ®): | 0.75 units per reaction |

The primers used are:

```
Casein4      5'-CCTTCTTTCCAGGATGAACTCCAGG-3'           (SEQ ID NO: 2)

CaseinDde2   5' GAGTAAGAGGAGGGATGTTTTGTGGGAGGCTCT-3'  (SEQ ID NO: 1)
```

PCR was carried out on an MJ Research PTC200 (hot bonnet) using the following protocol:

| | | |
|---|---|---|
| 1 cycle | 94.0° C. 4 min | |
| 35 cycles | 94.0° C. 30 sec | Denature |
| | 60.0° C. 30 sec | Anneal |
| | 72.0° C. 30 sec | Extend |
| 1 cycle | 72.0° C. 4 min | |
| end 4.0° C. | | |

Following PCR, restriction enzyme cocktail (10 μl) was added and the mixture incubated at 37° C. overnight. The restriction enzyme cocktail was prepared according to the following:

| Components | Final Concentration |
|---|---|
| Dde 1 10 U/μl (GibcoBRL ®) | 4.5 units per reaction |
| REACT ® 3 (GibcoBRL ®) | 25 mM Tris-HCl (pH 8.0), 5.0 mM MgCl$_2$, 50 mM NaCl |

The amplification product (10 μl) was analysed by electrophoresis (80V, 1 hour) in ethidium bromide stained agarose gel (3%, 1×TBE).

Figure 6:
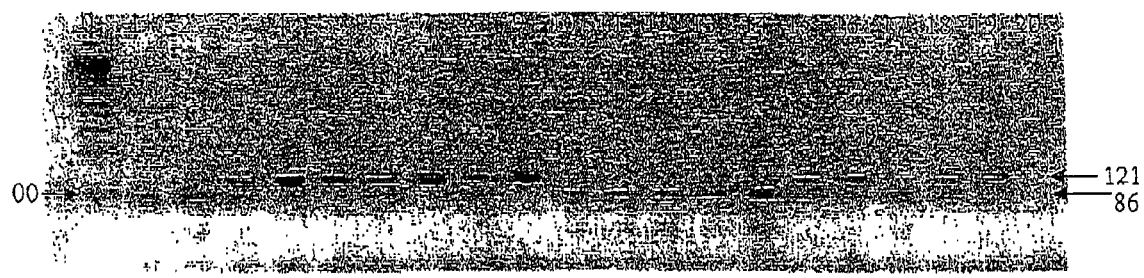
FIG. 6 shows the electrophoresis results for the ACRS genotyping method.

FIG. 6 shows the results of 20 samples analysed by the procedure outlined above.

A size standard ladder was loaded in position 0. The 100 bp band is identified in FIG. 6. The negative control (no DNA) was loaded in position 20. Samples homozygous for CT at positions 2 and 3 of codon 67 of the β-casein gene result in a single 86 bp band when cut by Dde1. This is shown in load positions 1, 2, 10, 11, 12, 13, 14 and 17.

Samples not containing CT at positions 2 and 3 of codon 67 of the β-casein gene are not cut by Dde1, leaving a single 121 bp band. This is shown in load positions 4, 5, 7 and 9.

Heterozygous samples result in both cut (86 bp) and uncut (121 bp) bands. This is shown in load positions 3, 6, 8, 15, 16, 18 and 19. Because of heteroduplex formation, the uncut band (121 bp) is expected to be more intense than the cut band (86 bp).

Example 2

Primer Extension Method

DNA extracts from hair follicles were prepared using the method described in Example 1. Alternatively, genomic DNA isolated by other methods can be used at a concentration at about 2.5 ng/μl.

A DNA sample (1 μl) from each of 96 animals was placed into a 96 well PCR microtitre plate (or alternatively, from each of 384 animals into a 384 well PCR plate).

For the 96 well plate, a cocktail of the following reagents was prepared in a 1.5 ml microtube. The cocktail (4 μl) was added to each well in the plate with a repeating pipette.

| Reagent | Volume μl |
|---|---|
| Water (HPLC grade) | 222 |
| 10x Hotstar Taq PCR buffer containing 15 mM MgCl$_2$ | 50 |
| HotStar Taq Polymerase (5 U/μl) | 4 |
| 25 mM MgCl$_2$ | 20 |
| dNTP 25mM | 4 |
| Forward and reverse primer mix Forward: actggattatggactcaaagatttg (SEQ ID NO: 7) Reverse: aaggtgcagattttcaacat (SEQ ID NO: 8) (1 μM each primer) | 100 |

PCR was carried out using the following protocol:

| | |
|---|---|
| 1 cycle: | 95° C. 15 minutes |
| 45 cycles: | 95° C. 20 seconds |
| | 56° C. 30 seconds |
| | 72° C. 1 minute |
| 1 cycle: | 72° C. 3 minutes |
| end | 4° C. |

The following SAP solution was prepared in a 1.5 ml microtube:

| Reagent | Volume μl |
|---|---|
| Nanopure water | 792.54 |
| hME Buffer (Sequenom, San Deigo) | 88.06 |
| Shrimp alkaline phosphatase | 155.4 |

The solution was mixed well and centrifuged for ten seconds at 5000 RPM.

SAP solution (2 μl) was transferred to each well of the plate containing the samples. The plate was incubated using a thermocycler at 37° C. for 20 minutes, 85° C. for 5 minutes, and then holding at 4° C.

The following extension cocktail was prepared in a 1.5 μl microtube:

| Reagent | Volume μl |
|---|---|
| Nanopure Water | 895.11 μl |
| Sequenom 10x hME extend buffer with 2.25 mM ddA, ddC, ddT, dG | 103.6 μl |

-continued

| Reagent | Volume μl |
|---|---|
| Primer (100 uM) | 27.97 μl |
| RMA6 R: gttttgtgggaggctgtta (SEQ ID NO: 9) | |
| Thermosequenase (32 U/μl) | 9.32 μl |

The extension cocktail (2 μl) was added to each well of the sample plate. The plate was sealed and thermocycled as follows:

| 1 cycle: | 94° C. for 2 minutes |
|---|---|
| 40 cycles: | 94° C. for 5 seconds |
| | 52° C. for 5 seconds |
| | 72° C. for 5 seconds |
| End | 4° C. |

Prior to mass spectrometry the samples were cleaned using SpectroCLEAN and then analysed using MALDI-TOF MS.

Figure 8:
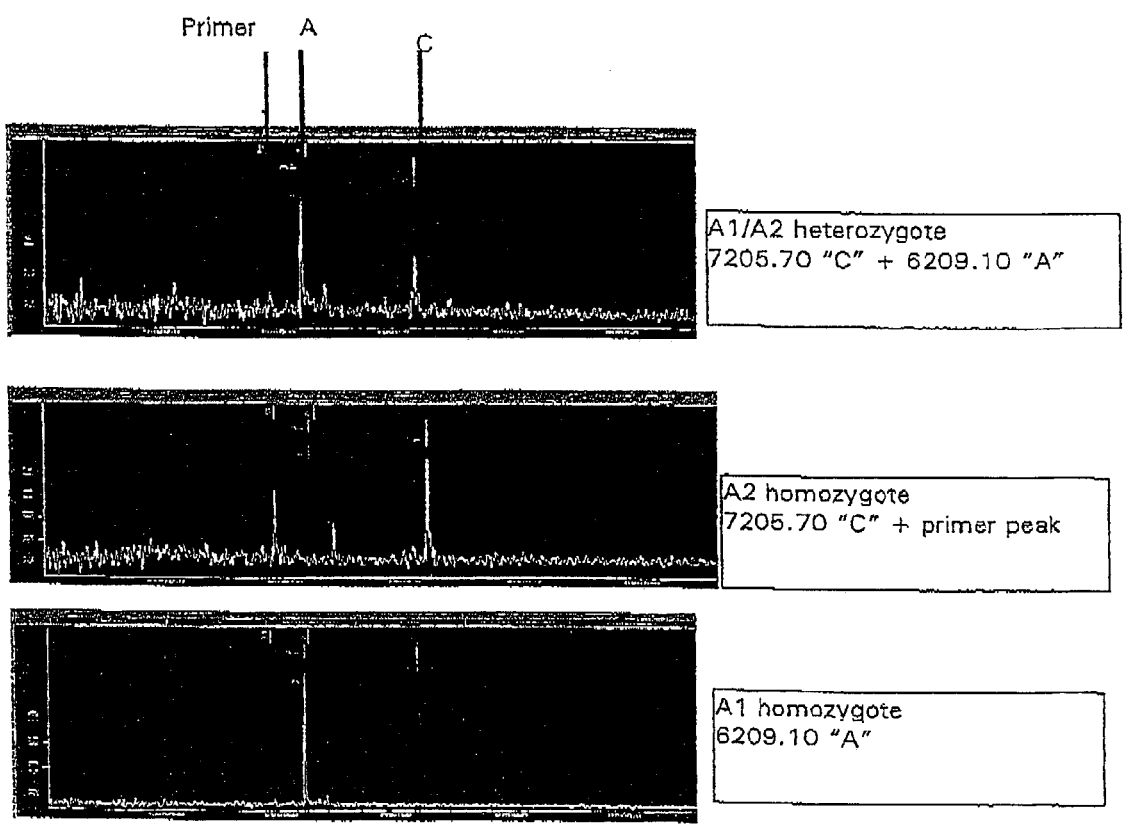
FIG. 8 shows mass spectrometry profile results for the Primer Extension genotyping method.
Figure 9:
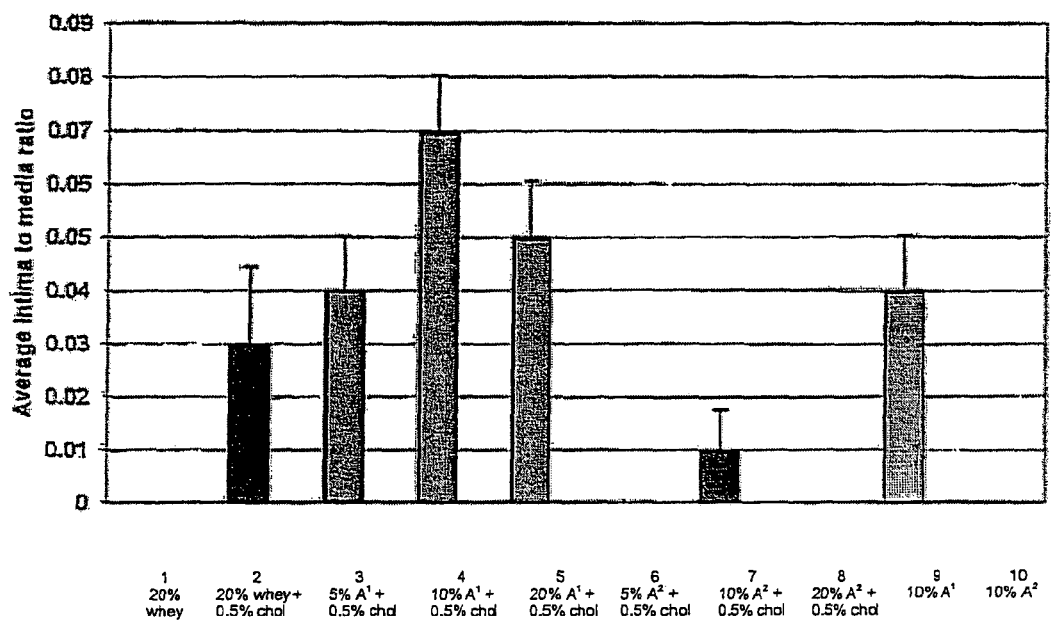
FIG. 9 shows average intima to media ratios (indicative of arterial thickening) of the aorta, for β-casein $A^2$, β-casein $A^1$ and whey-fed NZ white rabbits.
Figure 10:
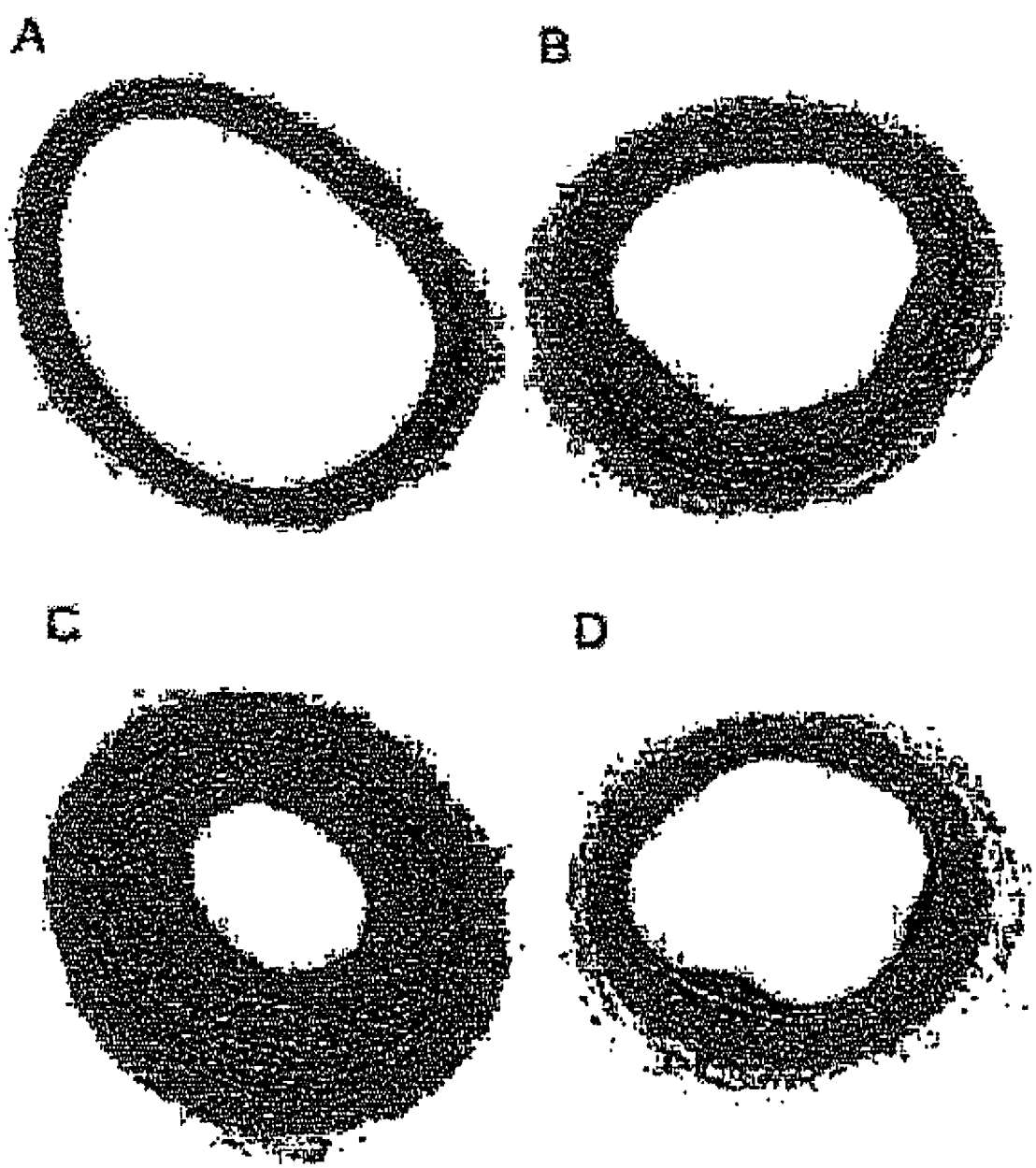
FIG. 10 shows the extent of neointimal thickening of the de-endothelialised right carotid artery (indicative of arterial disease progression following insult to arterial walls).
Figure 11:
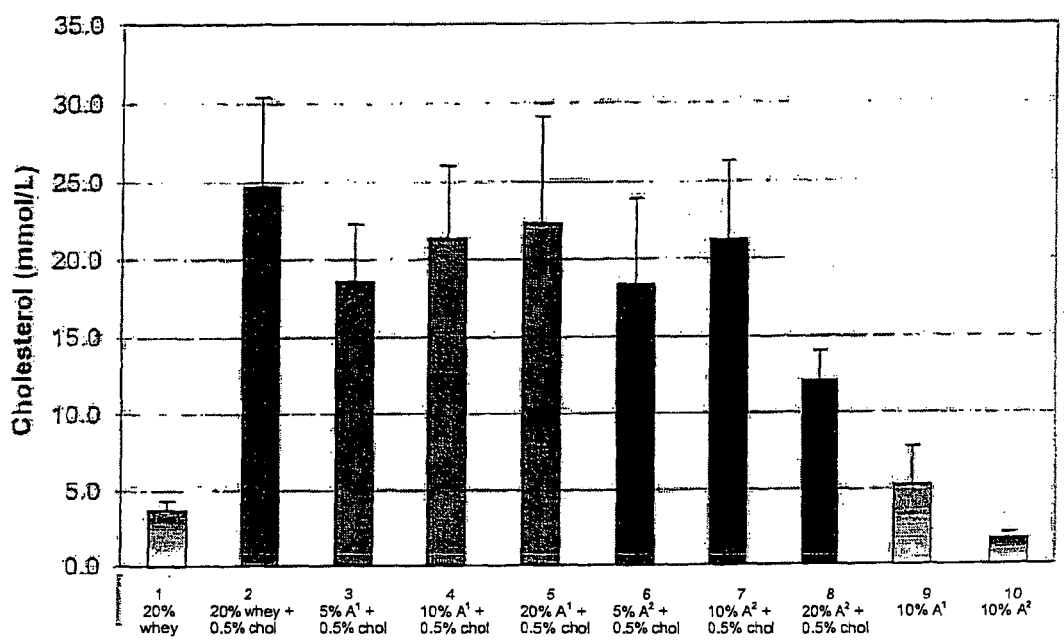
FIG. 11 shows serum cholesterol levels for β-casein $A^2$-fed, β-casein $A^1$-fed and whey-fed NZ white rabbits.
Figure 12:
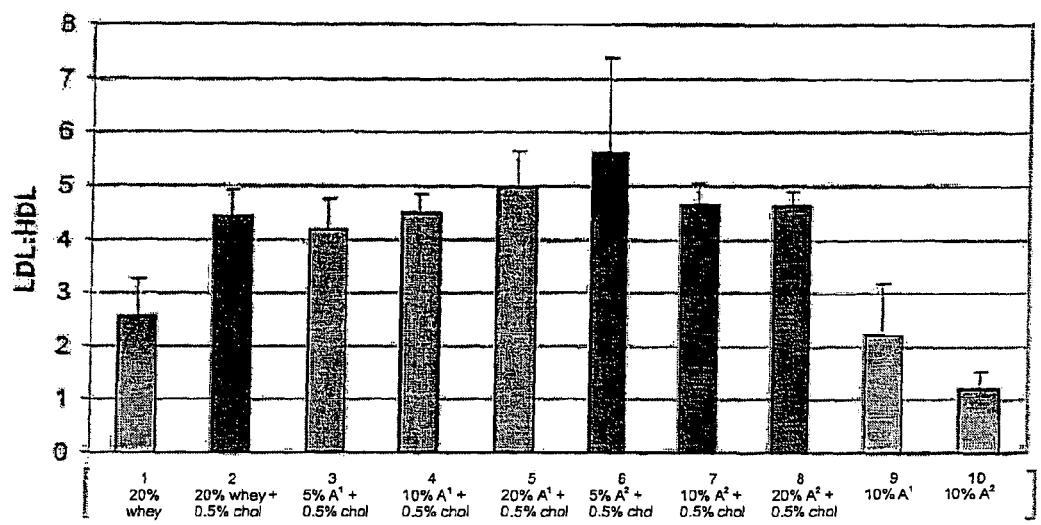
FIG. 12 shows serum LDL to HDL ratios for β-casein $A^2$-fed, β-casein $A^1$-fed and whey-fed NZ white rabbits.

The profiles obtained for homozygous and heterozygous animals for the CCT and CAT SNPs are shown in FIG. 8. The location of the primer, analyte A and analyte C extension products are shown.

Example 3

Rabbit Studies

Materials and Methods

Sixty New Zealand White/Lop cross rabbits of both sexes (16–24 weeks old) were obtained from the University of Queensland Central Animal Breeding House.

Protocol Summary

At time=0, the right carotid artery of all rabbits was balloon de-endothelialised. The rabbits were then randomly divided into 10 Groups and fed the specified diets for 6 weeks. Blood samples were taken at t=0, 3 and 6 weeks for analysis of serum constituents. At t=6 weeks, all animals were sacrificed and tissue samples taken. A summary of the study protocol is shown in Table 1.

Surgery

Figure 2:
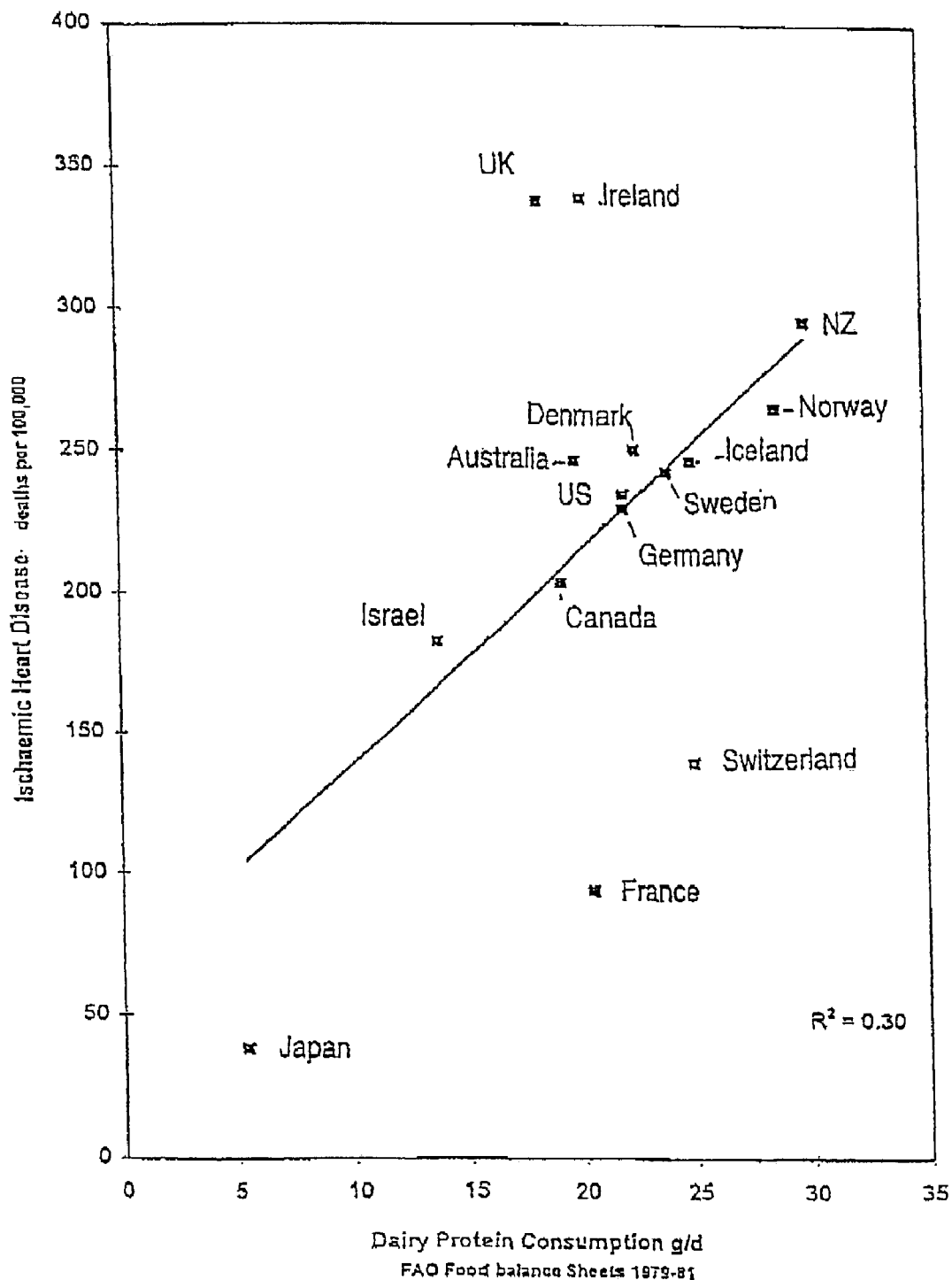
FIG. 2 is a graph showing the regression relationship between the death rate from Ischaemic heart disease (per 100,000 males aged 30–69 for the year 1985) and the estimated average daily intake of dairy protein per head of population over a number of countries.

At time=0, all 60 rabbits were anaesthetised with a mixture of ketamine (30 mg/kg) and xylazine (7 mg/kg) i.m. and maintained on Halothane (Laser Animal Health, Qld, Australia). An incision was made through skin and fascia, and blunt dissection and incision through the stylohyoid muscle exposed the upper part of the right common carotid artery. The left, uninjured common carotid artery served as a contralateral control. Side branches were temporarily ligated with 5/0 silk (Davis & Geck, Danbury, Conn., USA) and a 2 French (2F) Fogarty embolectomy catheter (Baxter Healthcare Corporation, Irvine, Calif., USA) was introduced through an arteriotomy made in the superior thyroid artery, a branch of the external carotid artery (FIG. 2.2). The catheter was advanced 10 cm (to the aortic arch), the balloon inflated with 0.2 ml of saline and the catheter withdrawn in order to deendothelialise the artery.

The injury procedure was performed three times in each animal to ensure complete removal of the endothelium. After injury, the catheter was removed, the superior thyroid artery ligated with 5/0 silk and the wound closed using 2/0 Dexon braided sutures (Sherwood Medical, St Louis, Mo., USA). A broad-spectrum antibiotic (5 mg/kg Baytril, Bayer Australia Ltd, Pymble, Australia) containing 50 mg/ml enrofloxacin was administered sub-cutaneously at the completion of the procedure. The rabbits were monitored post operatively and returned to their cages when fully conscious. For three days post-surgery each animal was gavaged with approximately 170 mg of paracetamol (SmithKline Beecham International, Ermington, Australia) and subcutaneous administration of antibiotics was continued.

Rabbit Diets

The study involved 10 diets, the compositions of which are shown in Table 2. Essentially, each diet contained 20% total milk protein, but differed in the proportion of casein protein to whey protein. Diets of Groups 1, 9 and 10 contained no further additives, while diets of Groups 2, 3, 4, 5, 6, 7 and 8 were supplemented with 0.5% cholesterol. There were 6 rabbits in each group and the diet was continued for 6 weeks.

TABLE 5

| | Protocol Summary | | | | | | |
|---|---|---|---|---|---|---|---|
| Week | 0 | 1 | 2 | 3 | 4 | 5 | 6 |
| Surgery | X | | | | | | |
| Diet | XXXXXXX | XXXXXXX | XXXXXXX | XXXXXXX | XXXXXXX | XXXXXXX | XXXXXXX |
| Bleeds | X | | | X | | | X |
| Weights | X | X | X | X | X | X | X |
| Sacrifice | | | | | | | X |

Surgery at t = 0;
study pellets distributed daily;
blood collection at t = 0, 3, 6 weeks;
weights recorded weekly;
sacrifice at t = 6 weeks

TABLE 6

Compositions of study diets offered to rabbits for 6 weeks

Ingredients (grams/kg)

| Diet Group | 1 | 2 | 3 | 4 | 5 | 6 | 7 | 8 | 9 | 10 |
|---|---|---|---|---|---|---|---|---|---|---|
| β-casein A[1] | 0 | 0 | 50 | 100 | 200 | 0 | 0 | 0 | 100 | 0 |
| β-casein A[2] | 0 | 0 | 0 | 0 | 0 | 50 | 100 | 200 | 0 | 100 |
| Whey protein | 228 | 228 | 171 | 113.8 | 0 | 171 | 113.8 | 0 | 113.8 | 113.8 |
| Cholesterol | 0 | 5 | 5 | 5 | 5 | 5 | 5 | 5 | 0 | 0 |
| DL-Methionine | 3 | 3 | 3 | 3 | 3 | 3 | 3 | 3 | 3 | 3 |
| Sucrose | 426.372 | 421.372 | 428.53 | 435.886 | 449.865 | 428.496 | 435.818 | 449.865 | 440.886 | 440.886 |
| Corn Oil | 10 | 10 | 10 | 10 | 10 | 10 | 10 | 10 | 10 | 10 |
| Coconut Oil | 130 | 130 | 130 | 130 | 130 | 130 | 130 | 130 | 130 | 130 |
| Cellulose, Fibre | 150 | 150 | 150 | 150 | 150 | 150 | 150 | 150 | 150 | 150 |
| Salt Mix #200951 | 40 | 40 | 40 | 40 | 40 | 40 | 40 | 40 | 40 | 40 |
| Vitamin Mix #320005 | 10 | 10 | 10 | 10 | 10 | 10 | 10 | 10 | 10 | 10 |
| Chollne Bitartrate | 2 | 2 | 2 | 2 | 2 | 2 | 2 | 2 | 2 | 2 |
| Zinc premix (5 mg/g) | 0.628 | 0.628 | 0.47 | 0.314 | 0.135 | 0.504 | 0.382 | 0.135 | 0.314 | 0.314 |
| Total | 1000 | 1000 | 1000 | 1000 | 1000 | 1000 | 1000 | 1000 | 1000 | 1000 |

It was found that it took several days for the rabbits to become accustomed to their new diets, which differed from their normal pellets in colour, smell, texture and weight. Pellets fed in the new diets were white, while normal pellets are brown. Thus, for five days prior to surgery, all rabbits were weaned onto their respective diets by mixing increasing amounts of the new pellets (25%, 50%, 75%, 100%) with normal rabbit pellets (to total 200 grams). At t=0, only new pellets (200 grams per day) were offered (exceptions, see below) for the following 6 weeks and water was available ad libitum. It is known that rabbits eat 90–130 grams of pellets per day. However, 200 grams was required to fill the hopper such that the animals could reach the food. A fresh 200 grams of pellets was provided daily and the amount of pellets left uneaten by each rabbit was determined by weighing each day.

Several measures were employed to encourage the rabbits to eat the new diet. Firstly, a small amount of aniseed oil was dropped onto the back of the food hoppers to stimulate the rabbits' appetites. Secondly, if a rabbit was still not eating its new diet or its weight loss was approaching 10% of original body weight, normal food was added to the diet at 25, 50 or 75% mixtures. When this occurred, the white diet pellets were carefully separated from the brown normal pellets and weighed each day to determine the actual amount of experimental diet consumed. Finally, if the weight loss continued, the rabbits were offered 200 grams of normal food per day until their body weight increased.

Rabbit Weights

All rabbits were weighed weekly, commencing the day of surgery, until the week of sacrifice.

Blood Collection

Blood was collected from each rabbit prior to surgery, at the commencement of diet and at t=3 and 6 weeks. Each rabbit was wrapped securely and the fur covering the central ear artery was shaved. A 24 gauge catheter (Becton Diskinson Pty Ltd, NSW, Australia) was inserted and 5 mL of blood was collected into sterile tubes. The blood was allowed to clot and was centrifuged at 4500 rpm for 10 minutes. The serum supernatant was extracted and analysed for total serum cholesterol, triglycerides, HDL, LDL and homocysteine.

Rabbit Sacrifice

Six weeks after injury, 1000 I.U. heparin (David Bull Laboratories, Mulgrave, Victoria) in 1 ml saline were injected into an ear vein of each rabbit. Five minutes later, the rabbits were euthanased with an overdose of pentobarbitone (325 mg/ml Lethabarb, (Virbac Australia Pty Ltd, Victoria)). An incision was made from the chin to pelvis and continued to the hindlimbs and forelimbs. The peritoneal cavity was then carefully incised to expose internal organs and the rib cage was cut away to expose the heart. The left ventricle was cannulated with a wide gauge needle attached to tubing which was in turn connected to a perfusion apparatus. A small section of the inferior vena cava was cleared and severed. The circulatory system was flushed with 1 litre of Dulbecco's Phosphate Buffered Saline (DPBS) before arterial perfusion fixation was performed with 1 liter of 4% formaldehyde (Asia Pacific Speciality Chemicals Ltd, NSW, Australia) in DPBS at 100 mm Hg.

Tissue Collection

The entire aorta, from the iliac bifurcation to the aortic arch, was exposed and removed. The right (injured) and the left (control) common carotid arteries were fully exposed and removed. All vessels were cleaned of fat and adherent connective tissue before being placed into tubes with 4% formaldehyde in DPBS.

Tissue Analysis

En Face Oil-Red-O Staining for Luminal Lesions

The aortic arch was removed for fixation and histological sectioning. The remainder of the aorta (approximately 16 cm) was opened longitudinally and cut into four segments. Each segment was sewn (lumen side up) onto small pieces of clear plastic to ensure they remained flat. The segments were then stained en face in a saturated solution of the lipophilic dye Oil Red O to enable determination of luminal surface area covered by fatty streaks.

Analysis of Luminal Surface Area Covered by Fatty Streaks

Images of each aortic segment were scanned using Desk Scan II (version 2.31a, Hewlett-Packard, U.S.A.) and the total lesion area was measured using the ImageJ imaging software (version 1.23y, National Institute of Health, U.S.A.). This program compares the intensity of the lesions (stained bright red) against the rest of the arterial surface (white to pale pink). The results were expressed as the percentage of surface area covered by lesions.

Aortic Arch

Three segments of approximately 3–4 mm in length were cut from each aortic arch and placed in DPBS for two washes of 30 minutes each. The segments were then dehydrated in increasing concentrations of ethanol, i.e. 70% ethanol for 30 minutes, then 95% ethanol for 30 minutes and finally, 100% ethanol for three washes of 30 minutes each. They were then placed in the first of two infiltration resin solutions (Technovit 7100, Heraeus, Germany) and left on a rotator overnight. The segments were then transferred to the second resin solution and were again left on a rotator overnight. Each segment was then carefully placed upright into embedding moulds, held in place by a minimal amount of superglue at the base of the mould. The same resin mixture used for infiltration was mixed with a hardener and this was pipetted into the mould until all segments were completely covered. The plastic was left to polymerise at room temperature for two hours before being placed into a 37° C. oven overnight. The plastic blocks were then gently removed from their moulds and mounted onto Histoblocks, using Technovit 3040 (Heraeus, Germany) as glue. Each block was securely fitted to the microtome (LKB Bromma, Germany) and trimmed by cutting approximately 60–70 sections of 10 μm each. These were discarded and the microtome was set to cut 5 μm sections. These sections were collected with forceps and stretched in distilled water held at room temperature. They were then collected onto glass slides and dried for approximately 15 minutes at 60° C. The sections were then stained for 10 minutes with Toluidine Blue before being washed four times with tap water and allowed to air dry.

Right and Left Carotid Arteries

Four and five segments, each approximately 3–4 mm in length, were cut from the left (control) and the right (ballooned) carotid arteries respectively. A different number of sections was used in the control and the experimental vessels, to avoid confusion between tissues during embedding and sectioning. The segments were dehydrated, embedded, sectioned and stained using the method previously described for the aortic arch segments.

Intima to Media Ratios

All morphometric analyses of the intima to media ratios (I:M) of the ballooned and control carotid arteries and the aortic arch were perfomed using the Mocha Image Analysis system (version 1.1, Jandel Scientific, Ca., U.S.A.). Measurements were taken to determine the size (in pixels) of both the intima and media layers in all segments of each artery. Using an Excel (Microsoft Corporation, N.Y., U.S.A.) spreadsheet, the ratio of intima to media was calculated and recorded for each of the three aortic arch segments per rabbit, the four control carotid segments and the five ballooned carotid segments.

Statistics

All statistical analyses were performed using the SigmaStat (Jandel Scientific, Ca., U.S.A.) statistical software package. Comparison of data from the morphometric analyses were carried out with One-Way Multiple ANOVAs, using the "Kruskal-Wallis" Analysis of Variance on Ranks test. Extreme outliers were identified using Tukey's Outlier Test. In all statistical analyses a P value of less than 0.05 was considered significant. The information has been presented graphically using Microsoft Excel (Microsoft Corporation, N.Y., U.S.A.). All data has been reported as mean±standard error of mean.

Results

Rabbit Diets

Rabbits were weaned onto their respective new diets for a few days prior to t=0, and some animals whose weight loss approached 10% had their diet supplemented with normal pellets for a few days. Thus it was essential to measure the amount of new pellets eaten by each animal per day by providing a known weight (200 grams) of fresh pellets each morning and weighing the uneaten portion the following morning immediately prior to offering 200 grams of fresh pellets. Where a mixture of new pellets (white) and normal pellets (brown) was offered, the two were separated prior to weighing.

The weight of the white pellets eaten by each rabbit varied between rabbits. On group averages, the weight of pellets consumed only varied by 12 grams per day over the six week experimental period and ranged from 23.2 grams to 35.3 grams per day (mean 30.48±0.97 grams). There was no significant difference in the amount of diet pellets eaten between any of the Groups. The addition of 0.5% cholesterol to the diets of Groups 2–8 did not influence the amount eaten, nor did the type or amount of casein. Thus, while the amount of food consumed by the rabbits was relatively low (mean 30.48 grams white pellets per day, mean 10.22 grams brown pellets per day, total mean 40.72 grams per day) resulting in some weight loss, the amount of the new diet consumed in each Group was relatively constant and thus results between Groups can be compared.

Rabbit Weights

Almost all rabbits lost weight over 6 weeks, with only Group 9 (10% $A^1$ without added cholesterol) recording an average weight gain of 2.15±1.2%. Group 10 rabbits (10% $A^2$ without added cholesterol) showed only a small weight loss of −0.92±0.97%. Group 1 rabbits on 20% whey only (no added cholesterol) lost 4.5±6% of their original body weight over the 6 week study, while the remaining Groups 2–8 (all with added cholesterol) lost mean 7.57±4.72% of their original body weight.

The greatest mean weight loss was by Group 6. However this was entirely due to one rabbit (K6) that had a large starting weight of 3.81 kg. This rabbit ate an average of 21.58 grams of pellets per day, approximately 9 grams per day less than the mean of all rabbits (30.50). K6 showed no sign of illness and at the time of sacrifice and all organs appeared normal with the exception of a very small liver of normal colour. The remaining five rabbits in this Group lost less than 5% of their original body weight. There was no apparent relationship between proportion or type of casein on weight change.

Effect of Diet on Cholesterol

At week 6 cholesterol levels of almost all Groups were significantly different from Group 1 (20% whey only). Interestingly, the cholesterol level in Group 9 ($A^1$) was higher than in Group 1, but this was not significant. Also, the cholesterol level in Group 8 (20% $A^2$ with cholesterol) was approximately half of that produced from 20% whey with added cholesterol (Group 2), although this too was not significant. Group 9 serum cholesterol was significantly lower than all Groups that had dietary cholesterol (Groups 2–8). Group 10 ($A^2$) serum cholesterol was significantly lower than in Group 1, and indeed was significantly lower than that in all groups, including Group 9.

The results indicate that addition to 0.5% cholesterol to the diet has caused an increase in serum cholesterol levels irrespective of the amount of whey in the diet and both the amounts and types of casein. Also, in the absence of dietary cholesterol, $A^2$ produced lower serum cholesterol levels than both $A^1$ and whey.

Effect of Diet on Triglycerides

By week 6 triglyceride levels from Groups 5 (20% $A^1$) and 9 (10% $A^1$ without added cholesterol) had increased from week 0 and Groups 4 (10% $A^1$) and 10 (10% $A^2$ without added cholesterol) had shown no change. The serum triglyceride levels for all other Groups had fallen from those at week 0.

Effect of Diet on LDL

In all groups with added dietary cholesterol, serum LDL levels were significantly higher than Group 1 (whey alone) or Groups 9 ($A^1$) and 10 ($A^2$) with no dietary cholesterol. Group 9 ($A^1$ with no dietary cholesterol) was not significantly different from Group 1, but Group 10 ($A^2$ with no dietary cholesterol) was significantly lower. Also Group 10 LDL levels were significantly lower than those for Group 9. All Groups with added dietary cholesterol (Groups 2–8) were not significantly different from each other.

Thus, serum LDL levels followed the same pattern as serum cholesterol and indicate that addition of dietary cholesterol has increased serum LDL levels in all appropriate groups, while the $A^2$ casein variant in the absence of dietary cholesterol, produced lower serum LDL than either $A^1$ or whey alone.

Effect of Diet on HDL

Serum HDL followed the same pattern as serum LDL with added dietary cholesterol (Groups 2–8) causing significantly elevated levels than those with no added cholesterol (Groups 1, 9 and 10). Group 9 was not significantly different from Group 1, but was significantly higher than Group 10, which in turn was significantly lower than all Groups except Group 1. β-Casein $A^2$ without dietary cholesterol produced a lowered serum HDL level than $A^1$.

Effect of Diet on LDL to HDL Ratio

The LDL to HDL ratios were determined by dividing the individual rabbit's serum LDL levels by the same rabbit's serum HDL levels. The mean LDL:HDL for each Group was then determined. It was found that the LDL:HDL of Group 10 (10% β-casein $A^2$ alone) was significantly lower than all other groups including whey alone and β-casein $A^1$ alone. The LDL to HDL ratios of all Groups with dietary cholesterol (Groups 2–8) were not significantly different from each other. As with the serum LDL and HDL levels, there was a trend for higher levels with higher doses of β-casein $A^1$ and lower levels with higher doses of β-casein $A^2$.

Effect of Diet on Homocysteine

By week 6, serum homocysteine levels had changed only slightly from those at week 0 with no significant difference demonstrated between the experimental groups.

Effect of Diet on Atherosclerosis

Group 1 rabbits fed 20% whey had 0% aortic surface area covered by plaque. All other Groups had some plaque, including those from Group 10, although this was not significantly higher than Group 1. Only Groups 1 and 10 were significantly lower than Group 3, which was also considerably higher than Groups 2–9, however, variation between rabbits within this Group was great, with a range between 2.8 and 18.4%. Three rabbits were excluded from these calculations as they were deemed extreme outliers.

Group 1 thoracic aorta had 0% of the surface area covered by fatty streaks. All other Groups had some lesions, including Groups 9 ($A^1$) and 10 ($A^2$) with no dietary cholesterol. Groups 9 and 10 were not significantly different from each other. For both $A^1$ and $A^2$ with dietary cholesterol, there was a trend to lower percent lesions with increasing concentration of casein variant, but this was not significant. Group 3 was considerably higher than all others, but not significantly different. Of the six rabbits in this Group, three had a high percentage of surface area covered by plaque and three had low values.

The abdominal aorta isolated from animals fed $A^2$ in the absence of dietary cholesterol (Group 10) had only minimal surface area covered by plaque and was not significantly different from Group 1 (whey only) which had 0% covered by plaque. Group 10 was significantly lower than all other Groups including Group 9 ($A^1$, no dietary cholesterol). Group 3 (5% $A^1$ with dietary cholesterol) was significantly higher than Group 2 with 20% whey and dietary cholesterol.

Thus, both casein variants without dietary cholesterol produce more extensive fatty streaks than whey alone but $A^2$ is less atherogenic than $A^1$. In addition, $A^1$ is more atherogenic than $A^2$ in the presence of dietary cholesterol.

Intima to Media Ratios

With 20% whey alone (Group 1) there was no intimal thickening of the aortic arch. Similarly, in the presence of 10% $A^2$ with no dietary cholesterol (Group 10) or with dietary cholesterol and 5% or 20% $A^2$ (Groups 6 and 8), the mean intima to media ratio was 0. Group 7 (10% $A^2$ with dietary cholesterol) had a mean intima to media ratio of only 0.01, with four of the six rabbits having 0%. All $A^1$ groups (both with and without dietary cholesterol) had higher intima to media ratios than groups fed $A^2$ casein and had intima to media ratios not significantly different from Group 2 (20% whey with 0.5% cholesterol). Indeed, 10% $A^1$ in the absence of dietary cholesterol produced the same intima to media ratio as 20% whey with 0.5% whey with 0.5% dietary cholesterol (0.03).

Thus, in relation to the thickness of fatty streak lesions in the aortic arch, $A^1$ casein, even in the absence of dietary cholesterol, produces lesions similar to that produced by 0.5% cholesterol. In contrast $A^2$, both in the presence and absence of dietary cholesterol, appears to be highly atheroprotective.

Balloon catheter injury to the right carotid artery t=0 induced a hyperplastic neointimal thickening in all rabbits by 6 week. Measurement of intima to media ratios showed there was a slight, but not significant increase in neointimal thickening in Group 2 rabbits (20% whey with 0.5% cholesterol) compared with Group 1 (20% whey alone). Likewise, the groups fed 5, 10 and 20% $A^1$ plus 0.5% cholesterol had thicker, but not significantly different neointimas than Group 1. Groups fed 5, 10 and 20% $A^2$ plus 0.5% cholesterol all had thinner neointimas than their $A^1$ counterparts, but again this was not significant. Similarly, in the absence of dietary cholesterol the intima to media ratio in $A^2$ fed animals (Group 10) was lower than in the $A^1$-fed Group 9.

There was no neointimal thickening observed in all of the control vessels.

INDUSTRIAL APPLICATION

The invention provides a useful food product capable of increasing the health of an individual, or the health of a population. The invention relates to a method of preventing or treating coronary heart disease in a human population which derives some of its food intake from milk or other dairy products by reducing or substantially eliminating the presence of β-casein $A^1$ within the diet of that population.

REFERENCES

1. Aleandri, R., Buttazzoni, L. G., Schneider, J. C., Caroli, A., and Davoli, R. (1990) J. Dairy Sci., 73, 241–255.
2. Annand, J. C. (1967) J. Atheroscl., 7, 798–801.
3. Aschaffenburg, R. (1961) Nature, 192, 431–432.
4. Bassette, R., and Acosta, J. S. (1988) Fundamentals of Dairy Chemistry, $3^{rd}$ Ed.,—Chapter 1: Composition of Milk (Ed. Wong, N. P.) Van Nostrand Reinhold, New York, pp 1–38.
5. Beales, P. E., Elliot, R. B., Flohe, S., Hill, J. P., Kolb, H., Pozzilli, P., Wang, G. -S., Wasmuth, H., and Scott, F. W. (2002) Diabetologia, 45, 1240–1246.
6. Bovenhuis, H., van Arendonk, J. A. M., and Korver, S. (1992) J. Dairy Sci., 75, 2549–2559.
7. Eigel, W. N. (1984) J. Dairy Sci., 67, 1599–1631.
8. Gonyon, D. S., Mather, R. E., Hines, H. C., Haenlein, G. F. W., Arave, C. W., and Gaunt, S. N. (1987) J. Dairy Sci., 70, 2585–2598.
9. Heinecke, J. W. (1999) FASEB J., 13, 1113–1120.
10. Jakob, E. and Puhan, Z. (1997) Bulletin of the IDF, 304, pp 2–3 and 6–8.
11. Jinsmaa, Y. and Yoshikawa, M. (1999) Peptides, 20, 957–962.
12. Laugesen, M., and Elliot, R. (2003) NZ Med. J., 116, 1168.
13. McLachlan, C. N. S. (2001) Med. Hypotheses, 56, 262–272.
14. McLean, D. M., Graham, E. R. B., Ponzoni, R. W., and McKenzie, H. A. (1984) J. Dairy Res., 51, 531–546.
15. Ng-Kwai-Hang, K. F., Monardes, H. G., and Hayes, J. E., (1990) J. Dairy Sci., 73, 3414–3420.
16. Peterson, R. F., and Kopfler, F. C. (1966) Biochem. Biophys. Res. Commun., 22, 388–392.
17. Steinberg, D., Parthasarathy, S., Carew, T. E., Khoo, J. C. and Witzum, J. L. (1989) N. Engl. J. Med., 320, 915–924.
18. Torreilles, J. and Guerin, M. C. (1995) French Compt. Rendu Seances Soc. Biol. Filial, 189, 933–945.

The invention claimed is:

1. A method of producing milk from one or more lactating bovines producing milk substantially free of β-casein A$^1$ but comprises at least one or more of β-caseins A$^2$, A$^3$, B, C, D and E, the method comprising the steps of:
   (i) breeding one or more bovine bulls that are known not to have DNA encoding for β-casein A$^1$ with bovine cows that do not have DNA encoding for β-casein A$^1$ to give progeny cows which do not have DNA encoding β-casein A$^1$; and
   (ii) milking the progeny cows.

2. The method as claimed in claim 1 including the step of testing DNA or RNA from cells obtained from each of the bovine cows for the presence of DNA or RNA encoding β-casein A$^1$.

3. The method as claimed in claim 2 when the DNA or RNA obtained from each of the bovine cows is obtained from blood, hair, or skin of the bovine cows.

4. The method as claimed in claim 1 including the step of testing DNA or RNA from cells obtained from the one or more bovine bulls for the presence of DNA or RNA encoding any of β-caseins A$^1$, B, C and F.

5. The method as claimed in claim 4 where the DNA or RNA obtained from the one or more bovine bulls is obtained from semen, blood, hair, or skin of the one or more bovine bulls.

6. The method as claimed in claim 1 including the step of testing DNA or RNA from cells obtained from each of the bovine cows for the presence of DNA or RNA encoding any of β-caseins A$^1$, B, C and F.

7. The method as claimed in claim 6 when the DNA or RNA obtained from each of the bovine cows is obtained from blood, hair, or skin of the bovine cows.

8. The method as claimed in claim 1 including the step of testing DNA or RNA from cells obtained from the one or more bovine bulls for the presence of DNA or RNA encoding β-casein $A^2$.

9. The method as claimed in claim 8 where the DNA or RNA obtained from the one or more bovine bulls is obtained from semen, blood, hair, or skin of the one or more bovine bulls.

10. The method as claimed in claim 1 including the step of testing DNA or RNA from cells obtained from each of the bovine cows for the presence of DNA or RNA encoding β-casein $A^2$.

11. The method as claimed in claim 10 when the DNA or RNA obtained from each of the bovine cows is obtained from blood, hair, or skin of the bovine cows.

12. The method as claimed in claim 1 including the step of testing milk obtained from each of the bovine cows for the presence of β-casein $A^1$.

13. The method as claimed in claim 1 where the breeding of the one or more bovine bulls with the bovine cows is by natural insemination or is by artificial insemination.

14. The method as claimed in claim 1 where the one or more bovine bulls and the bovine cows are *Bos taurus* bovines.

15. The method as claimed in claim 1 where the β-casein contained in the milk produced comprises β-casein $A^2$ in the amount greater than 95% by weight of the β-caseins in the milk.

16. The method as claimed in claim 1 where the β-casein contained in the milk produced comprises β-casein $A^2$ in the amount approximately 100% by weight of the β-caseins in the milk.

17. A method of producing milk from one or more lactating bovines producing milk substantially free of β-casein $A^1$ but comprises at least one or more of β-caseins $A^2$, $A^3$, B, C, D and E, the method comprising the steps of:

(i) breeding one or more bovine bulls that are known not to have DNA encoding for β-casein $A^1$ with bovine cows that do not have DNA encoding for β-casein $A^1$ to give progeny cows which do not have DNA encoding β-casein $A^1$; and (ii) milking the progeny cows, and wherein said one or more bovine bulls are known not to have DNA encoding for β-casein $A^1$ are determined by testing DNA or RNA from cells obtained from one or more bovine bulls for the presence of DNA or RNA encoding β-casein $A^1$.

18. The method as claimed in claim 17 where the DNA or RNA obtained from the one or more bovine bulls is obtained from semen, blood, hair, or skin of the one or more bovine bulls.

19. A method of producing milk from one or more lactating bovines producing milk substantially free of β-casein $A^1$ but comprises at least one or more of β-caseins $A^2$, $A^3$, B, C, D and E, the method comprising the steps of:

(i) breeding one or more bovine bulls that are known not to have DNA encoding for β-casein $A^1$ with bovine cows that are known not to have DNA encoding for β-casein $A^1$ to give progeny cows which do not have DNA encoding β-casein $A^1$; and (ii) milking the progeny cows.

* * * * *

SEQUENCE LISTING

```
<160> NUMBER OF SEQ ID NOS: 14

<210> SEQ ID NO 1
<211> LENGTH: 33
<212> TYPE: DNA
<213> ORGANISM: Artificial Sequence
<220> FEATURE:
<223> OTHER INFORMATION: Made in lab.

<400> SEQUENCE: 1
gagtaagagg agggatgttt tgtgggaggc tct                              33

<210> SEQ ID NO 2
<211> LENGTH: 25
<212> TYPE: DNA
<213> ORGANISM: Artificial Sequence
<220> FEATURE:
<223> OTHER INFORMATION: Made in lab.

<400> SEQUENCE: 2
ccttctttcc aggatgaact ccagg                                       25

<210> SEQ ID NO 3
<211> LENGTH: 19
<212> TYPE: DNA
<213> ORGANISM: Artificial Sequence
<220> FEATURE:
<223> OTHER INFORMATION: Made in lab.

<400> SEQUENCE: 3
gttttgtggg aggctgtta                                              19

<210> SEQ ID NO 4
<211> LENGTH: 20
```

```
<212> TYPE: DNA
<213> ORGANISM: Artificial Sequence
<220> FEATURE:
<223> OTHER INFORMATION: Made in lab.

<400> SEQUENCE: 4
gttttgtggg aggctgttag                                                    20

<210> SEQ ID NO 5
<211> LENGTH: 20
<212> TYPE: DNA
<213> ORGANISM: Artificial Sequence
<220> FEATURE:
<223> OTHER INFORMATION: Made in lab.

<400> SEQUENCE: 5
gttttgtggg aggctgttat                                                    20

<210> SEQ ID NO 6
<211> LENGTH: 23
<212> TYPE: DNA
<213> ORGANISM: Artificial Sequence
<220> FEATURE:
<223> OTHER INFORMATION: Made in lab.

<400> SEQUENCE: 6
gttttgtggg aggctgttag gga                                                23

<210> SEQ ID NO 7
<211> LENGTH: 25
<212> TYPE: DNA
<213> ORGANISM: Artificial Sequence
<220> FEATURE:
<223> OTHER INFORMATION: Made in lab.

<400> SEQUENCE: 7
actggattat ggactcaaag atttg                                              25

<210> SEQ ID NO 8
<211> LENGTH: 20
<212> TYPE: DNA
<213> ORGANISM: Artificial Sequence
<220> FEATURE:
<223> OTHER INFORMATION: Made in lab.

<400> SEQUENCE: 8
aaggtgcaga ttttcaacat                                                    20

<210> SEQ ID NO 9
<211> LENGTH: 19
<212> TYPE: DNA
<213> ORGANISM: Artificial Sequence
<220> FEATURE:
<223> OTHER INFORMATION: Made in lab.

<400> SEQUENCE: 9
gttttgtggg aggctgtta                                                     19

<210> SEQ ID NO 10
<211> LENGTH: 46
<212> TYPE: DNA
<213> ORGANISM: Artificial Sequence
<220> FEATURE:
<223> OTHER INFORMATION: Made in lab.

<400> SEQUENCE: 10
```

```
gagtaagagg agggatgttt tgtgggaggc tcttagggat gggccc                    46
```

<210> SEQ ID NO 11
<211> LENGTH: 46
<212> TYPE: DNA
<213> ORGANISM: Artificial Sequence
<220> FEATURE:
<223> OTHER INFORMATION: Made in lab.

<400> SEQUENCE: 11

```
gagtaagagg agggatgttt tgtgggaggc tcttagggat gggccc                    46
```

<210> SEQ ID NO 12
<211> LENGTH: 319
<212> TYPE: DNA
<213> ORGANISM: Artificial Sequence
<220> FEATURE:
<223> OTHER INFORMATION: Made in lab.

<400> SEQUENCE: 12

```
actggattat ggactcaaag atttgttttc cttctttcca ggatgaactc cggataaaat     60
ccaccccttt gcccagacac agtctctagt ctatcccttc cctgggccca tccmtaacag   120
cctcccacaa aacatccctc ctcttactca aaccctgtg gtggtgccgc ctttccttca   180
gcctgaagta atgggagtct ccaaagtgaa ggaggctatg gctcctaagc amaaagaaat   240
gcccttccct aaatatccag ttgagccctt tactgaaags cagagcctga ctctcactga   300
tgttgaaaat ctgcacctt                                                319
```

<210> SEQ ID NO 13
<211> LENGTH: 56
<212> TYPE: DNA
<213> ORGANISM: Bos sp.

<400> SEQUENCE: 13

```
cccttgggcc catccctaac agcctcccac aaaacatccc tcctcttact caaacc        56
```

<210> SEQ ID NO 14
<211> LENGTH: 56
<212> TYPE: DNA
<213> ORGANISM: Bos sp.

<400> SEQUENCE: 14

```
cccttgggcc catccataac agcctcccac aaaacatccc tcctcttact caaacc        56
```